(12) United States Patent
Dai et al.

(10) Patent No.: US 12,247,202 B2
(45) Date of Patent: Mar. 11, 2025

(54) CIRCULAR RNAS AND PREPARATION METHODS THEREOF

(71) Applicant: EXCLCIRC (SUZHOU) BIOMEDICAL CO., LTD., Jiangsu (CN)

(72) Inventors: Dongsheng Dai, Suzhou (CN); Lynn Shan, Suzhou (CN); Zilin Dai, Suzhou (CN)

(73) Assignee: EXCLCIRC (SUZHOU) BIOMEDICAL CO., LTD., Suzhou (CN)

( * ) Notice: Subject to any disclaimer, the term of this patent is extended or adjusted under 35 U.S.C. 154(b) by 3 days.

(21) Appl. No.: 18/464,200

(22) Filed: Sep. 9, 2023

(65) Prior Publication Data

US 2024/0093185 A1    Mar. 21, 2024

(30) Foreign Application Priority Data

Sep. 10, 2022  (CN) .......................... 202211105849.6
May 17, 2023  (CN) .......................... 202310557196.3

(51) Int. Cl.
| | |
|---|---|
| *C12N 15/11* | (2006.01) |
| *C07K 14/195* | (2006.01) |
| *C12N 9/22* | (2006.01) |
| *C12N 15/63* | (2006.01) |

(52) U.S. Cl.
CPC ............ *C12N 15/11* (2013.01); *C07K 14/195* (2013.01); *C12N 9/22* (2013.01); *C12N 15/63* (2013.01)

(58) Field of Classification Search
CPC ........ C12N 2840/203; C12N 2310/532; C12N 2830/42; C12N 15/87; C12N 15/11; A61K 47/549
See application file for complete search history.

(56) References Cited

U.S. PATENT DOCUMENTS

| | | | |
|---|---|---|---|
| 2016/0083747 A1 | 3/2016 | Kruse | |
| 2020/0080106 A1 | 3/2020 | Anderson et al. | |
| 2022/0177910 A1* | 6/2022 | Sun | ........................ C12N 15/85 |
| 2022/0323480 A1* | 10/2022 | Goodman | ............ A61K 9/0019 |

FOREIGN PATENT DOCUMENTS

| | | |
|---|---|---|
| CN | 109097395 A | 12/2018 |
| CN | 112399860 A | 2/2021 |

OTHER PUBLICATIONS

Rausch et al., Characterization and circumventing sequence restrictions for synthesis of circular RNA in vitro, Nucleic Acids Research, vol. 49, No. 6, e35, pp. 1-13. (Year: 2021).*
International Search Report in PCT/CN2023/117889 mailed on Dec. 9, 2023, 4 pages.
Written Opinion in PCT/CN2023/117889 mailed on Dec. 9, 2023, 3 pages.
Chen, Xinjie et al., Circular RNA: Biosynthesis in Vitro, Frontiers in Bioengineering and Biotechnology, 2021, 11 pages.
R. Alexander Wesselhoeft et al., Engineering Circular RNA for Potent and Stable Translation in Eukaryotic Cells, Nature Communications, 2018, 10 pages.

* cited by examiner

*Primary Examiner* — Dana H Shin
(74) *Attorney, Agent, or Firm* — METIS IP LLC

(57) ABSTRACT

DNA molecules for making a circular RNA are provided. The DNA molecule may include elements operably connected and arranged, from a 5' to 3' direction, in the following order: (a) an intron fragment that includes a full-length intron; (b) an E2 fragment which includes a downstream exon of the full-length intron; and (c) an E1 fragment which includes an upstream exon of the full-length intron. 3' end of the E1 fragment is configured to produce a hydroxyl group in an in vitro transcription reaction; the hydroxyl group is capable of initiating splicing in a one-step transesterification reaction at a splice site between RNA fragments transcribed from the intron fragment and the E2 fragment in a linear RNA that is produced from the DNA molecule in the in vitro transcription reaction, such that the linear RNA is configured to self-circularize to produce the circular RNA.

6 Claims, 34 Drawing Sheets

Specification includes a Sequence Listing.

SEQ ID NO. 2
AAAATCCGTTGACCTTAAACGGTCGTGTGGGTTCAAGTCCCTCCACCCCCA ▇ Left Exon_51
SEQ ID NO. 3
AAAATCCGTTGACCTTAAACGGTCGTGTGGGTTCAAGTCC ▇ Left Exon_40
SEQ ID NO. 4
AAAATCCGTTGACCTTAAACGGTCGTGTGG ▇ Left Exon_30
SEQ ID NO. 5
AAAATCCGTTGACCTTAAAC ▇ Left Exon_20

AAAATCCG ▇ Left Exon_8

AAAATC ▇ Left Exon_6

AAAA ▇ Left Exon_4

AA ▇ Left Exon_2

FIG. 9

Right Exon_15    AGACGCTACGGACTT    SEQ ID NO. 8

Right Exon_10    CTACGGACTT    SEQ ID NO. 9

Right Exon_6    GGACTT

Right Exon_4    ACTT

Right Exon_2    TT

FIG. 13

Process

1. Performing an IVT reaction (a concentration of $Mg^{2+}$ being 44 Mm)

2. Digesting a transcription template with DNase I enzyme

3. Chelating the $Mg^{2+}$ with different concentrations of EDTAs

4. Digesting a linear RNA with RNase R enzyme

CIRCULAR RNAS AND PREPARATION METHODS THEREOF

CROSS-REFERENCE TO RELATED APPLICATIONS

This application claims priority to Chinese Patent Application No. 202211105849.6, filed on Sep. 10, 2022, and Chinese Patent Application No. 202310557196.3, filed on May 17, 2023, the entire contents of each of which are incorporated herein by reference.

SEQUENCE LISTING

The instant application contains a Sequence Listing which has been submitted electronically in XML format and is hereby incorporated by reference in its entirety. The XML copy, created on Sep. 12, 2024, is named "Sequence Listing-20917-0001US00" and is 23,799 bytes in size.

TECHNICAL FIELD

The present disclosure relates to the field of molecular biology, in particular, to applications and preparation methods of circular RNAs.

BACKGROUND

Circular ribonucleic acids (circRNAs) are an important class of the regulatory non-coding RNA. A circRNA usually includes an enclosed circular structure, and is generally not affected by RNA exonucleases. CircRNAs are often stable in nature and can regulate gene expression through a variety of mechanisms.

At present, circRNAs can be divided into three categories: exonic circular RNAs formed based on an exon by back splicing; intronic circular RNAs formed based on an intron region by a process of debranch inhibition; and exon-intron circular RNAs formed based on an exon and an intron. Researchers have found the presence of the circRNAs in viruses, yeast, fruit flies, nematodes, mice, monkeys, and humans. Due to the enclosed structure of the circRNAs, these molecules can accumulate continuously due to their stability and have the capability of avoiding degradation.

The disclosed circularization methods in prior art are too complex and require a large number of enzymes. For example, translatable or biologically active circRNA is generated in a eukaryotic cell through two consecutive steps of transesterification with the help of the homologous arm; moreover, the circRNA is mainly purified using size exclusion chromatography (SEC) or other methods based on molecular weight differences between the reaction products (e.g., the circRNA and a precursor linear RNA of the circRNA). However, due to the minimal difference between molecular weights of the circRNA and the linear RNA, the purification of the circRNA pose extensive challenges (e.g., not efficient in separating circRNA from the linear RNA present in the reaction products).

Therefore, it is desirable to provide preparation methods of circRNAs that can minimize circularization operations, reduce the requirement of raw materials, lower the production costs, enhance the circularization efficiency, and improve the purification effect.

SUMMARY

An aspect of the present disclosure provides a DNA molecule for making a circular RNA. The DNA molecule include elements operably connected and arranged, from a 5' to 3' direction, in the following order:
 (a) an intron fragment that includes a full-length intron;
 (b) an E2 fragment which includes a downstream exon of the full-length intron; and
 (c) an E1 fragment which includes an upstream exon of the full-length intron.

In some embodiments, the full-length intron, the downstream exon, and the upstream exon may be from a same gene; 3' end of the E1 fragment may be configured to produce a hydroxyl group in an in vitro transcription reaction. The hydroxyl group may be capable of initiating splicing in a one-step transesterification reaction at a splice site between RNA fragments transcribed from the intron fragment and the E2 fragment in a linear RNA that is produced from the DNA molecule in the in vitro transcription reaction, such that the linear RNA may be configured to self-circularize to produce the circular RNA.

In some embodiments, the DNA molecule may not include any intron sequence at the 3' end of the E1 fragment.

In some embodiments, the DNA molecule further include a target fragment positioned between the E2 fragment and the E1 fragment. The target fragment may include a target DNA sequence that encodes a target peptide.

In some embodiments, the target fragment may be a gene of interest (GOI) fragment, and the nucleotide sequence of the GOI fragment is capable of being transcribed into a target RNA sequence.

In some embodiments, the GOI fragment encodes a protein coding RNA sequence or a non-coding RNA sequence.

In some embodiments, the DNA molecule further include an internal ribosome entry site (IRES) fragment positioned between the E2 fragment and the E1 fragment. The IRES fragment may be transcribed to an RNA molecule that is capable of recruiting ribosomes for a translation reaction to obtain a target peptide.

In some embodiments, the IRES fragment may be from: Taura syndrome virus, *Triatoma* virus, Thayer's encephalomyelitis virus, simian virus 40, *Solenopsis invicta* virus 1, *Rhopalosiphum padi* virus, reticuloendotheliosis virus, Forman poliomyelitis virus 1, *Plautia stali* intestine virus, Kashmir bee virus, human rhinovirus 2, Homalodisca coagulata virus-1, human immunodeficiency virus type 1, Homalodisca coagulata virus-1, Himetobi P virus, hepatitis C virus, hepatitis A virus, hepatitis B virus, foot-and-mouth disease virus, human enterovirus 71, equine rhinovirus, *Ectropis obliqua*-like virus, Encephalomyocarditis virus (EMCV), *Drosophila* C virus, Cruciferae tobacco virus, cricket paralysis virus, bovine viral diarrhea virus 1, black queen cell virus, aphid lethal paralysis virus, avian encephalomyclitis virus, acute bee paralysis virus, Hibiscus Chlorotic Ringspot virus, hog cholera virus, human FGF2, human SFTPA1, human AML1/RUNX1, *Drosophila* antenna, human AQP4, human AT1R, human BAG-1, human BCL2, human BiP, human c-IAPI, human c-myc, human elF4G, mouse NDST4L, human LEF1, mouse HIF1α, human n.myc, mouse Gtx, human p27kipl, human PDGF2/c-sis, human p53, human Pim-1, mouse Rbm3, *Drosophila* reaper, dog Scamper, *Drosophila* Ubx, salivary virus, Coxsackie virus, Parechovirus, human UNR, mouse UtrA, human VEGF-A, human XIAP, *Drosophila* hairless, *Saccharomyces cerevisiae* TFIID, *Saccharomyces cerevisiae* YAP1, human c-src, human FGF-1, Simian picornavirus, turnip crinkle virus, aptamer of elF4G, Coxsackie virus B1, Coxsackie virus B2, or Coxsackie virus B3 (CVB3).

In some embodiments, the DNA molecule further include a 5' homology arm sequence and a 3' homology arm sequence positioned between the E2 fragment and the E1 fragment.

In some embodiments, the DNA molecule may not include a 5' homology arm sequence or a 3' homology arm sequence positioned between the E2 fragment and the E1 fragment when the length of the target DNA sequence that encodes the target peptide is less than 2000 nt.

In some embodiments, the gene may include a td gene of a T4 phage or a pre-tRNA$_{Leu}$ gene of genus *Anabaena*, and the td gene may have a nucleotide sequence shown in SEQ ID NO. 18, the pre-tRNA$_{Leu}$ gene has a nucleotide sequence shown in SEQ ID NO. 19.

In some embodiments, the E2 fragment may be an exon sequence comprising 8-51 bases in size; and the E1 fragment may be an exon sequence comprising 2-15 bases in size.

In some embodiments, the E2 fragment may be an exon sequence downstream of an intron of the pre-tRNA$_{Leu}$ gene of genus *Anabaena*; and the E1 fragment may be an exon upstream sequence of the intron fragment of the pre-tRNA$_{Leu}$ gene of genus *Anabaena*.

In some embodiments, the nucleotide sequence of the intron fragment may have at least 95% similarity with SEQ ID NO. 1, the nucleotide sequence of the E2 fragment may have at least 95% similarity with any one sequence of SEQ ID NO. 2 to SEQ ID NO. 5 and sequences AAAATCCG, AAAATC, AAAA, and AA, the nucleotide sequence of the E1 fragment may have at least 95% similarity with any one sequence of SEQ ID NO. 8 to SEQ ID NO. 11 and sequences GGACTT, ACTT, TT, and CTT.

In some embodiments, the nucleotide sequence of the intron fragment may have the sequence shown in SEQ ID NO. 1; the nucleotide sequence of the E2 fragment may have the sequence shown in any one sequence of SEQ ID NO. 2 to SEQ ID NO. 5 and sequences AAAATCCG, AAAATC, AAAA, and AA; and the nucleotide sequence of the E1 fragment may have the sequence shown in any one sequence of SEQ ID NO. 8 to SEQ ID NO. 11 and sequences GGACTT, ACTT, TT, and CTT.

In some embodiments, the intron fragment may be further preceded by a promoter element, the promoter element may be one of a T7 promoter, a T3 promoter, and an SP6 promoter.

In some embodiments, the DNA molecule may further include a poly X fragment before the full-length intron fragment. The poly X fragment may include at least 7 identical consecutive bases, and the X is one or two of A, C, G, T, and U.

In some embodiments, the DNA molecule may be a vector.

Another aspect of the present disclosure provides a method for preparing the circular RNA based on the DNA molecule according to above embodiments. The method may include performing the in vitro transcription reaction, to obtain the linear RNA based on the DNA molecule; and allowing the linear RNA to self-circularize to produce the circular RNA.

In some embodiments, the DNA molecule includes a gene of interest (GOI) fragment capable of being transcribed into a target RNA sequence.

In some embodiments, the DNA molecule may be generated by in vitro synthesis.

In some embodiments, the DNA molecule may be generated by: constructing a recombinant plasmid that includes a sequence of the DNA molecule; obtaining the DNA molecule by PCR amplifications with the recombinant plasmid as a template, using a forward primer and a reverse primer at the end of an E1 sequence.

In some embodiments, the DNA molecule may be generated by: constructing a recombinant plasmid that includes a sequence of the DNA molecule; digesting the recombinant plasmid with a type IIS or type II blunt restriction endonuclease to obtain the DNA molecule.

In some embodiments, the type IIS restriction endonuclease may include BspQ I, Bsa I, or BsmB I; the type II blunt restriction endonuclease includes Hpa I, Swa I, or Dra I.

In some embodiments, a reaction temperature of the in vitro transcription reaction may be 30° C.-50° C. and a reaction time of the in vitro transcription reaction may be 0.5 h-16 h.

In some embodiments, the in vitro transcription reaction may include: making a mixture in an in vitro transcription system to obtain a mixed mixture; conducting the in vitro transcription reaction of the mixed mixture at 37° C. for 2 h to obtain a reaction product.

In some embodiments, the mixture may include: nucleotides including ATP, CTP, GTP, and UTP, the DNA molecule, a buffer, T7 RNA polymerase, and nuclease-free water.

In some embodiments, the method may further include treating the reaction product with DNase I enzyme at 37° C. for 15 minutes, to remove the DNA molecule, and followed by an incubation step at 50° C. for 20 min.

In some embodiments, the buffer may include Tris-HCl, MgCl$_2$, DTT, spermidine, and the concentration of Mg$^{2+}$ may be at least 32 mM.

In some embodiments, the DNA molecule may further include a poly X fragment before the full-length intron fragment, wherein the X is one or two of A, C, G, T, and U; the poly X fragment may include at least 7 identical consecutive bases, and the method may further include obtaining purified circular RNA by using oligo dX affinity beads. In some embodiments, an oligo dT affinity bead is used when the poly X fragment is poly A; an oligo dA affinity bead is used when the poly X fragment is poly T; an oligo dG affinity bead is used when the poly X fragment is poly C; an oligo dC affinity bead is used when the poly X fragment is poly G; and an oligo dA affinity bead is used when the poly X fragment is poly U.

In some embodiments, the method may further include: adding DNase I enzyme to a reaction product of the in vitro transcription reaction to remove the DNA molecule; adding a chelating agent to the reaction product to remove Mg$^{2+}$; and adding RNase R to the reaction product to digest the linear RNA.

Another aspect of the present disclosure provides a method for producing a target peptide by translation. The method may include obtaining the circular RNA based on the method for preparing the circular RNA based on the DNA molecule according to above embodiments; transfecting a cell with the circular RNA; starting a translation reaction based on the circular RNA to produce a target peptide.

BRIEF DESCRIPTION OF THE DRAWINGS

The present disclosure is further illustrated in terms of exemplary embodiments, and these exemplary embodiments are described in detail with reference to the drawings. These embodiments are not restrictive. In these embodiments, the same number indicates the same structure, wherein:

FIG. 9 is a schematic diagram illustrating exemplary optimized E2 fragments of downstream exons of an intron of a pre-tRNA$_{Leu}$ gene of genus *Anabaena* according to some embodiments of the present disclosure, wherein a GOI fragment of a DNA molecule has the nucleotide sequence shown in SEQ ID NO. 7.

FIG. 13 is a schematic diagram illustrating exemplary optimized E1 fragments of upstream exons of an intron of a pre-tRNA$_{Leu}$ gene of genus *Anabaena* according to some embodiments of the present disclosure, wherein a GOI fragment of a DNA molecule has the nucleotide sequence shown in SEQ ID NO. 7;

FIG. 32 shows an exemplary process of chelating $Mg^{2+}$ by EDTA according to some embodiments of the present disclosure;

DETAILED DESCRIPTION

Figure 1:
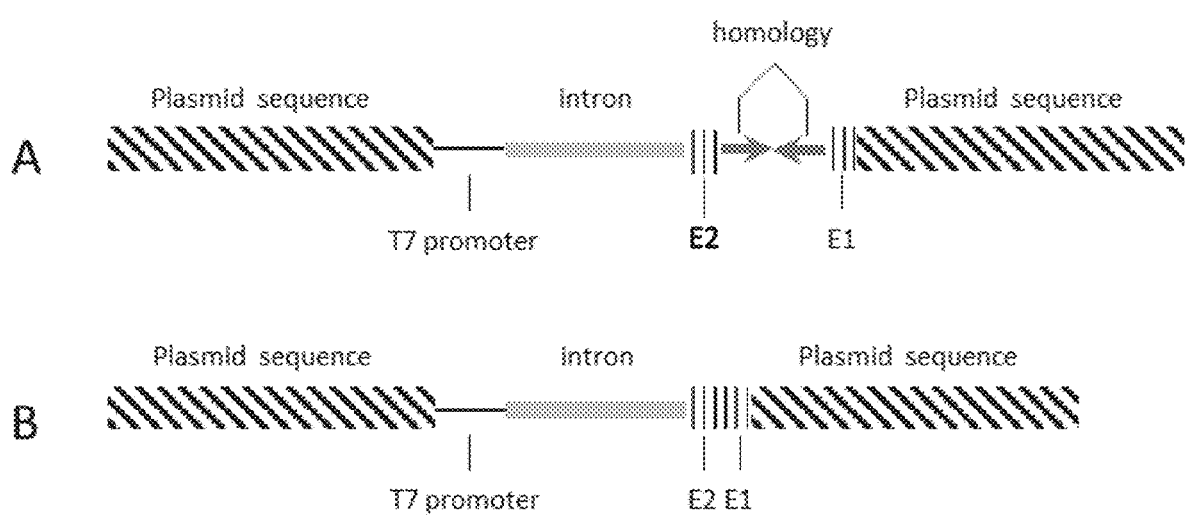
FIG. 1 is a pattern diagram illustrating an exemplary empty vector including a deoxyribonucleic acid (DNA) molecule that can make a circular ribonucleic acid (RNA) in an in vitro transcription reaction according to some embodiments of the present disclosure, wherein A in FIG. 1 is a pattern diagram including a homology arm sequence, and B in FIG. 1 is a pattern diagram not including a homology arm sequence.

In order to illustrate the technical solutions related to the embodiments of the present disclosure, a brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

As shown in the present disclosure and claims, unless the context clearly indicates exceptions, the words "a," "an," "one," and/or "the" do not specifically refer to the singular, but may also include the plural. The terms "including" and "comprising" only suggest that the steps and elements that have been clearly identified are included, and these steps and elements do not constitute an exclusive list, and the method or device may also include other steps or elements.

The flowcharts used in the present disclosure may illustrate operations executed by the system according to embodiments in the present disclosure. It should be understood that a previous operation or a subsequent operation of the flowcharts may not be accurately implemented in order. Conversely, various operations may be performed in inverted order, or simultaneously. Moreover, other operations may be added to the flowcharts, and one or more operations may be removed from the flowcharts.

Embodiments of the present disclosure provide a deoxyribonucleic acid (DNA) molecule for making a circular ribonucleic acid (RNA). The DNA molecule may include elements operably connected and arranged, from a 5' to 3' direction, in the following order:
  (a) an intron fragment that includes a full-length intron;
  (b) an E2 fragment which includes a downstream exon of the full-length intron; and
  (c) an E1 fragment which includes an upstream exon of the full-length intron.

As used herein, the "intron" refers to a non-coding fragment in a DNA sequence. The "exon" refers to a coding fragment in a DNA sequence, which can be transcribed and translated into a portion of the protein. The DNA sequence of a gene may include an intron and an exon. In a process of transcription, the gene is transcribed into an intermediate molecule, which is referred to as pre-messenger RNA (or linear RNA). In the pre-messenger RNA, an intron is transcribed, but it is not retained in a mature mRNA.

As used herein, "splicing" refers to a process that an intron is removed from the pre-messenger RNA, and an exon is connected to form a mature mRNA molecule. Splicing plays a significant role in regulating gene expression. The way and selectivity of the splicing may lead to various combinations of exons, leading to the production of multiple distinct mature mRNAs. Consequently, this process has an impact on the composition of proteins during transcription and translation.

As used herein, the "full-length intron" refers to a complete intron sequence extending from a starting boundary of an exon to an ending boundary of a next exon in a DNA sequence of a gene.

Although the intron does not directly encode proteins, the intron may play an important role in gene expression regulation, evolution, etc. By regulating and splicing, cells produce diverse proteins, thus adapting to different biological processes and environmental conditions.

As used herein, the "downstream exon" refers to an exon following an intron in a sequence of the pre-messenger RNA corresponding to a DNA sequence of a gene. The upstream exon is usually an exon before the downstream exon. The "upstream" and "downstream" are used herein to represent a spatial position of elements in a genome or an RNA sequence. For example, "upstream" refers to a direction farther away from an intron, while "downstream" refers to a direction closer to the intron.

As used herein, "transcription" refers to a process of synthesizing RNA using a DNA molecule as a template. Inside cellular structures, DNA carries the encoded biological genetic information. To effectively execute the biological genetic information in the cells, it is necessary to replicate the biological genetic information in the DNA into RNA molecules. This replication enables the production of proteins or the accomplishment of other functions during the translation process.

In the process of transcription, an enzyme known as RNA polymerase recognizes and binds a specific gene region in a DNA molecule. This enzyme can facilitate the synthesis of an RNA molecule using the DNA molecule as a template. This RNA is called the pre-messenger RNA (for Eukaryote). In the subsequent splicing process, the pre-messenger RNA may form a mature messenger RNA (mRNA) molecule by removing the intron (i.e., the non-coding sequence) and connecting the exon (i.e., the coding sequence) together. The mature mRNA molecule carries protein coding information and can be translated into proteins by a ribosome within a cell.

The process of transcription may be divided into an in vivo transcription and an in vitro transcription based on a transcription position. The in vivo transcription refers to a transcription process that occurs in a cellular environment of an organism. In the in vivo transcription, a DNA template may be recognized and combined by RNA polymerase to produce RNA molecules. The in vitro transcription refers to a transcription process in a simulated organism conducted in vitro and artificially created laboratory conditions. The in vitro transcription may be used to generate a large amount of RNA molecules for research and application, such as preparing RNA probes and studying the function of RNA molecules.

The circular RNA (circRNA) is a class of single stranded closed RNA molecule, which is produced by the pre-messenger RNA through an alternative splicing (AS, including exon circularization or intron circularization). An endogenous circRNA include a coding RNA or a non-coding RNA, does not contain a 5' end cap structure and 3' end polyA tail, and lacks a free end. Thus, the endogenous circRNA is not easy to be degraded by a nucleic acid exonuclease, and is more stable than a linear RNA. The comprehensive exploration of circular RNA relies on the utilization of in vitro preparation techniques to validate its biological functions. Among these methods, the in vitro circularization technique plays a crucial role.

Using a linear RNA as a precursor, the current common method of synthesizing circular RNA in an in vitro transcription reaction is to connect ends of two exons to form a covalently enclosed circular structure. The above process may be realized based on a chemical connection, an enzymatic connection, or a ribozyme splicing.

The chemical connection of linear RNAs may be realized by cyanogen bromide (BrCN) or 1-ethyl-3-(3-dimethylaminopropyl) carbodiimide (EDC).

In the enzymatic connection, there are three enzymes commonly used for RNA circularization: T4 DNA ligase 1 (T4 Dnl 1), T4 RNA ligase 1 (T4 Rnl 1), and T4 RNA ligase 2 (T4 Rnl 2). The above three enzymes for RNA circularization are ATP dependent. They catalyze the connection of 5'-phosphate and 3'-hydroxyl group at the end of a RNA through three nucleotide transfer steps, and connect two ends of exons of the linear RNA molecules to produce the circular RNA.

The ribozymes are a class of RNA with enzymatic catalysis, which are used in a permuted intron-exon (PIE) system based on type I intron or type II intron that can achieve RNA circularization. The PIE system utilizes either type I introns or type II introns with a self-splicing function to facilitate splicing. In the presence of magnesium ions and free GTP, this process results in the circularization of the intron and the fusion of intermediate sequences, ultimately generating circular RNA.

The self-splicing process of the PIE system, specifically the type I intron self-splicing, involves dividing an intron fragment and an auxiliary exon fragment into two parts within an RNA molecule. The 5' end sequence of the intron is transferred to one end of a target sequence, while the 3' end sequence is inserted at the other end of the target sequence. In the presence of GTP, the 3'-hydroxyl group of GTP initiates an attack on the splice site located at the 5' end of the intron sequence. This attack exposes a newly generated 3'-free hydroxyl group. The free hydroxyl group then proceeds to attack the splice site at the 3' end of the intron sequence, resulting in the generation of circular RNA. The PIE structure contributes to the self-circularization of the entire sequence except for the intron portion.

The self-splicing process of the PIE system, specifically the type II intron self-splicing, shares similarities with the type I intron self-splicing. However, there is a notable distinction. In the type II intron self-splicing, the 2'-hydroxyl group within the intron sequence initiates an attack on the splice site located at the 5' end of the intron sequence. This attack exposes a newly generated 3'-free hydroxyl group, which then proceeds to attack the splice site at the 3' end of the intron sequence, ultimately resulting in the production of circular RNA.

In other words, a splicing reaction involved in the type I intron or type II intron PIE system may take place through two steps of energy-independent transesterification. In the first step, the 3'-hydroxy group of the cofactor guanosine or the 2'-hydroxy group within the intron sequence initiates the reaction by acting on the 5' end of the intron so as to expose 3'-hydroxyl group at the end of the first exon. In the second step, the 3'-hydroxyl group generated at the end of the first exon acts on the splice site between the 3' end of the intron and the second exon.

In the present disclosure, it is described that during an in vitro transcription reaction, the RNA sequence corresponding to the E1 fragment, transcribed by a DNA molecule, can generate a hydroxyl group at one end. This hydroxyl group has the ability to initiate splicing in a one-step transesterification reaction at the splice site between the RNA fragments transcribed from the intron fragment and the E2 fragment. This process occurs within a linear RNA molecule that is produced from the DNA molecule during the in vitro transcription reaction. As a result, the linear RNA molecule is structured in a way that allows it to self-circularize and generate circular RNA. The formation of circular RNA does not require any additional attack or steps; only one transesterification step is needed to complete the circularization and obtain the desired circular RNA. This streamlined process reduces the complexity and number of operations involved in circularization.

In some embodiments, the full-length intron, the downstream exon, and the upstream exon may be from a same gene; a hydroxyl group may be produced at the 3' end of the E1 fragment in an in vitro transcription reaction. The hydroxyl group may be capable of initiating splicing in a one-step transesterification reaction at a splice site between RNA fragments transcribed from the intron fragment and the E2 fragment in a linear RNA that is produced from the DNA molecule in the in vitro transcription reaction, such that the linear RNA may be configured to self-circularize to produce the circular RNA.

In some embodiments, the gene of the full-length intron, the downstream exon, and the upstream exon may include a td gene of a T4 phage or a pre-tRNA$_{Leu}$ gene of genus *Anabaena*, and the td gene may have a nucleotide sequence shown in SEQ ID NO. 18, the pre-tRNA$_{Leu}$ gene may have a nucleotide sequence shown in SEQ ID NO. 19.

A longer exon may reduce the efficiency of splicing, because when dealing with the longer exon, splicing enzymes may take longer to deal with intron, thus increasing the risk of wrong splicing or inaccurate splicing. In addition, the longer exon may cause the complexity of splicing, because more splicing factors and proteins may be needed to coordinate the splicing process. On the contrary, a shorter exon may be easier to be treated by the splicing enzymes since the intron are shorter, and processing may be faster and more efficient, which may increase the accuracy and efficiency of splicing. Therefore, a length of an exon is one of the factors affecting the splicing efficiency.

In some embodiments, the E2 fragment may be an exon sequence comprising 8-51 bases in size; and the E1 fragment may be an exon sequence comprising 2-15 bases in size. In some embodiments, the E2 fragment may be an exon sequence comprising 20-51 bases in size. In some embodiments, the E2 fragment may be an exon sequence comprising 40-51 bases in size. In some embodiments, the E2 fragment may be an exon sequence comprising 8-40 bases in size. In some embodiments, the E2 fragment may be an exon sequence comprising 20-40 bases in size. In some embodiments, the E2 fragment may be an exon sequence comprising 8-20 bases in size. In some embodiments, the E2 fragment may be an exon sequence comprising 8, 10, 15, 20, 30, 40 or 50 bases in size.

In some embodiments, the E1 fragment may be an exon sequence comprising 2-10 bases in size. In some embodiments, the E1 fragment may be an exon sequence comprising 2-8 bases in size. In some embodiments, the E1 fragment may be an exon sequence comprising 2-6 bases in size. In some embodiments, the E1 fragment may be an exon sequence comprising 2-4 bases in size. In some embodiments, the E1 fragment may be an exon sequence comprising 4-8 bases in size. In some embodiments, the E1 fragment may be an exon sequence comprising 2, 4, 6, 8, 10, 12, or 15 bases in size.

In some embodiments, the E2 fragment may be an exon sequence downstream of an intron of the pre-tRNA$_{Leu}$ gene of genus *Anabaena*, and the E1 fragment is an exon sequence upstream of the intron fragment of the pre-tRNA$_{Leu}$ gene of genus *Anabaena*.

In some embodiments, a nucleotide sequence of the intron fragment may have at least 95% similarity with SEQ ID NO. 1, a nucleotide sequence of the E2 fragment may have at least 95% similarity with any one sequence of SEQ ID NO. 2 to SEQ ID NO. 5 and sequences AAAATCCG, AAAATC, AAAA, and AA, a nucleotide sequence of the E1 fragment may have at least 95% similarity with any one sequence of SEQ ID NO. 8 to SEQ ID NO. 11 and sequences GGACTT, ACTT, TT, and CTT. In some embodiments, the nucleotide sequence of the intron fragment may have 95%, 97%, 98%, or 99% similarity with SEQ ID NO. 1, a nucleotide sequence of the E2 fragment may have 95%, 97%, 98%, or 99% similarity with any one sequence of SEQ ID NO. 2 to SEQ ID NO. 5 and sequences AAAATCCG, AAAATC, AAAA, and AA, a nucleotide sequence of the E1 fragment may have 95%, 97%, 98%, or 99% similarity with any one sequence of SEQ ID NO. 8 to SEQ ID NO. 11 and sequences GGACTT, ACTT, TT, and CTT.

In some embodiments, the nucleotide sequence of the E2 fragment may have at least 95% similarity with any one sequence of SEQ ID NO. 2 to SEQ ID NO. 5 and sequences AAAATCCG. In some embodiments, the nucleotide sequence of the E2 fragment may have 95%, 97%, 98%, or 99% similarity with any one sequence of SEQ ID NO. 2 to SEQ ID NO. 5 and sequences AAAATCCG.

In some embodiments, the nucleotide sequence of the intron fragment may have the sequence shown in SEQ ID NO. 1; the nucleotide sequence of the E2 fragment may have the sequence shown in any one sequence of SEQ ID NO. 2 to SEQ ID NO. 5 and sequences AAAATCCG, AAAATC, AAAA, and AA; and the nucleotide sequence of the E1 fragment may have the sequence shown in any one sequence of SEQ ID NO. 8 to SEQ ID NO. 11 and sequences GGACTT, ACTT, TT, and CTT.

In some embodiments, the nucleotide sequence of the E2 fragment may have the sequence shown in any one sequence of SEQ ID NO. 2 to SEQ ID NO. 5 and sequences AAAATCCG.

In some embodiments, the DNA molecule may not include any intron sequence at the 3' end of the E1 fragment.

In some embodiments, the DNA molecule may further include a target fragment positioned between the E2 fragment and the E1 fragment. The target fragment may include a target DNA sequence that encodes a target peptide. In some embodiments, the target peptide may be a target protein. The target protein refers to a specific protein molecule that are studied, analyzed, or processed in research.

In some embodiments, after inserting a target fragment between the E2 fragment and the E1 fragment, an in vitro transcription template obtained based on the DNA molecule may form the circular RNA in the in vitro transcription reaction.

In some embodiments, the DNA molecule may include elements operably connected and arranged, from a 5' to 3' direction, in the following order:

(a) an intron fragment that includes a full-length intron;
(b) an E2 fragment which includes a downstream exon of the full-length intron;
(c) a gene of interest (GOI) fragment; and
(d) an E1 fragment which includes an upstream exon of the full-length intron.

In some embodiments, the target fragment may be the GOI fragment, and a nucleotide sequence of the GOI fragment is capable of being transcribed into a target RNA sequence. In some embodiments, the nucleotide sequence of the GOI fragment may have at least 95% similarity with SEQ ID NO. 6 or SEQ ID NO. 7. In some embodiments, a nucleotide sequence of the GOI fragment may have 95%, 97%, 98%, or 99% similarity with any one sequence of SEQ ID NO. 6 or SEQ ID NO. 7.

In some embodiments, the GOI fragment encodes a protein coding RNA sequence or a non-coding RNA sequence. In some embodiments, the nucleotide sequence of the GOI fragment may have the nucleotide sequence shown in SEQ ID NO. 6 or SEQ ID NO. 7.

In some embodiments, the DNA molecule may further include an internal ribosome entry site (IRES) fragment positioned between the E2 fragment and the E1 fragment, wherein the IRES fragment may be transcribed to an RNA molecule that is capable of recruiting ribosomes for a translation reaction to obtain the target peptide.

In some embodiments, the IRES fragment may be obtained from: Taura syndrome virus, *Triatoma* virus, Thayer's encephalomyelitis virus, simian virus 40, *Solenopsis invicta* virus 1, *Rhopalosiphum padi* virus, reticuloendotheliosis virus, Forman poliomyelitis virus 1, *Plautia stali* intestine virus, Kashmir bee virus, human rhinovirus 2, Homalodisca coagulata virus-1, human immunodeficiency virus type 1, Homalodisca coagulata virus-1, Himetobi P virus, hepatitis C virus, hepatitis A virus, hepatitis B virus, foot-and-mouth disease virus, human enterovirus 71, equine rhinovirus, *Ectropis obliqua*-like virus, Encephalomyocarditis virus (EMCV), *Drosophila* C virus, Cruciferae tobacco virus, cricket paralysis virus, bovine viral diarrhea virus 1, black queen cell virus, aphid lethal paralysis virus, avian encephalomyclitis virus, acute bee paralysis virus, Hibiscus Chlorotic Ringspot virus, hog cholera virus, human FGF2, human SFTPA1, human AMLI/RUNXI, *Drosophila* antenna, human AQP4, human AT1R, human BAG-1, human BCL2, human BiP, human c-IAPI, human c-myc, human eIF4G, mouse NDST4L, human LEF1, mouse HIF1α, human n.myc, mouse Gtx, human p27kipl, human PDGF2/c-sis, human p53, human Pim-1, mouse Rbm3, *Drosophila* reaper, dog Scamper, *Drosophila* Ubx, salivary virus, Coxsackie virus, Parechovirus, human UNR, mouse UtrA, human VEGF-A, human XIAP, *Drosophila* hairless, *Saccharomyces cerevisiae* TFIID, *Saccharomyces cerevisiae* YAP1, human c-src, human FGF-1, Simian picornavirus, turnip crinkle virus, aptamer of eIF4G, Coxsackie virus B1, Coxsackie virus B2, or Coxsackie virus B3 (CVB3).

In some embodiments, the IRES fragment may be from a IRES fragment of the CVB3. In some embodiments, the CVB3 may have the IRES fragment shown in SEQ ID NO. 14.

In some embodiments, the DNA molecule may include elements operably connected and arranged, from a 5' to 3' direction, in the following order:

(a) an intron fragment that includes a full-length intron;
(b) an E2 fragment which includes a downstream exon of the full-length intron;

(c) an IRES fragment; and
(d) an E1 fragment which includes an upstream exon of the full-length intron.

In some embodiments, after inserting a target fragment between the E1 fragment and the IRES fragment, an in vitro transcription template obtained based on the DNA molecule may form the circular RNA in the in vitro transcription reaction.

In some embodiments, the DNA molecule may further include a 5' homology arm sequence and a 3' homology arm sequence positioned between the E2 fragment and the E1 fragment.

The 5' homology arm sequence may be a sequence that matches a specific region in the target fragment. The 5' homology arm sequence may be usually positioned at the 5' end of the DNA molecule, and may perform a homologous recombination with the region in the target fragment.

The 3' homology arm sequence may be a sequence that matches another specific region in the target fragment. The 3' homology arm sequence may be usually positioned at the 3' end of the DNA molecule, and may perform a homologous recombination with another region in the target fragment.

In some embodiments, the DNA molecule may include elements operably connected and arranged, from a 5' to 3' direction, in the following order:
  (a) an intron fragment that includes a full-length intron;
  (b) an E2 fragment which includes a downstream exon of the full-length intron;
  (c) a 5' homology arm sequence;
  (d) a 3' homology arm sequence; and
  (e) an E1 fragment which includes an upstream exon of the full-length intron.

In some embodiments, after inserting a target fragment between the 5' homology arm sequence and the 3' homology arm sequence, an in vitro transcription template obtained based on the DNA molecule may form the circular RNA in the in vitro transcription reaction.

In some embodiments, the DNA molecule may include elements operably connected and arranged, from a 5' to 3' direction, in the following order:
  (a) an intron fragment that includes a full-length intron;
  (b) an E2 fragment which includes a downstream exon of the full-length intron;
  (c) a 5' homology arm sequence;
  (d) a IRES fragment;
  (e) a GOI fragment;
  (f) a 3' homology arm sequence; and
  (g) an E1 fragment which includes an upstream exon of the full-length intron.

In some embodiments, the 5' homology arm sequence and the 3' homology arm sequence may help to ensure a correct localization of the DNA molecule in a target genome or improve the efficiency of the circularization reaction of a long RNA sequence. By using these homology arm sequences in the transgenic technology, specific genes or DNA fragments may be inserted into a genome at a specific position of a target organism, thereby achieving the regulation of gene expression and function.

In some embodiments, the DNA molecule may not include a 5' homology arm sequence or a 3' homology arm sequence positioned between the E2 fragment and the E1 fragment when a length of the target DNA sequence that encodes the target peptide is less than 2000 nt.

In some embodiments, the DNA molecule may include elements operably connected and arranged, from a 5' to 3' direction, in the following order:
  (a) an intron fragment that includes a full-length intron;
  (b) an E2 fragment which includes a downstream exon of the full-length intron;
  (c) an IRES fragment;
  (d) a GOI fragment; and
  (e) an E1 fragment which includes an upstream exon of the full-length intron.

In some embodiments of the present disclosure, an in vitro transcription template obtained based on the DNA molecule may form the circular RNA in the in vitro transcription reaction, without the need of additional homology arm sequences, while ensuring the circularization efficiency, reducing the raw materials required for the in vitro circularization process, and reducing the production costs.

In some embodiments, the intron fragment may further be preceded by a promoter element, and the promoter element may one of a T7 promoter, a T3 promoter, and an SP6 promoter.

In some embodiments, the DNA molecule may further include a poly X fragment before the full-length intron fragment. The poly X fragment may include at least 7 identical consecutive bases, and the X is one or two of A, C, G, T, and U.

In some embodiments, the poly X fragment may be used for affinity adsorption by oligo dX affinity beads, to purify the circular RNA generated in the in vitro transcription reaction, thus obtaining high-purity circular RNA by using the oligo dX affinity beads. In some embodiments, the DNA molecule may be a vector.

As used herein, the "vector" refers to a tool used to carry, replicate, and express an exogenous DNA molecule or RNA molecule. In the context of transcription in the present disclosure, the vector refers to a molecule used to carry an exogenous DNA fragment and undergo a transcription reaction in a cell to produce an RNA.

The vector is usually a circular DNA molecule, such as a plasmid or a virus (e.g., adenovirus, Adeno-associated virus, etc.), bacterial artificial chromosome (BAC), yeast artificial chromosome (YAC), etc. These vectors have the ability to self-replicate and may replicate independently in cells, while also may carry exogenous genes such as protein coding genes and RNA genes, or the like.

In some embodiments, the vector may be designed to include a specific promoter, a regulatory element, and a terminator to allow the exogenous DNA within the cell to transcribe and produce the RNA. These RNA molecules may be mRNAs for encoding proteins or other non-coding RNAs.

In some embodiments, an in vitro transcription template may be obtained based on the above-mentioned vector, and the circular RNA may be formed in the in vitro transcription reaction based on the in vitro transcription template.

The in vitro transcription template may be obtained through various methods. For example, the in vitro transcription template may be directly obtained through an artificial in vitro synthesis. In some embodiments, the in vitro transcription template may be obtained by constructing plasmids for PCR amplification, or by cutting plasmids with a restriction endonuclease.

Embodiments of the present disclosure provide a method for preparing the circular RNA based on the DNA molecule mentioned above. In some embodiments, the method may include performing the in vitro transcription reaction, to obtain the linear RNA based on the DNA molecule; and allowing the linear RNA to self-circularize to produce the circular RNA.

In some embodiments, the DNA molecule is generated by in vitro synthesis.

In some embodiments, the DNA molecule is generated by: constructing a recombinant plasmid that includes a sequence of the DNA molecule; and obtaining the DNA molecule by PCR amplifications with the recombinant plasmid as a template, using a forward primer and a reverse primer at the end of an E1 sequence.

In some embodiments, the DNA molecule is generated by: constructing a recombinant plasmid that includes a sequence of the DNA molecule; and digesting the recombinant plasmid with a type IIS or type II blunt restriction endonuclease to obtain the DNA molecule.

In some embodiments, the type IIS restriction endonuclease may include BspQ I, Bsa I, or BsmB I; the type II blunt restriction endonuclease may include Hpa I, Swa I, or Dra I.

In some embodiments, a reaction temperature of the in vitro transcription reaction may be 30° C.-50° C., and a reaction time of the in vitro transcription reaction may be 0.5 h-16 h.

In some embodiments, the reaction temperature of the in vitro transcription reaction may be 30° C.-40° C. In some embodiments, the reaction temperature of the in vitro transcription reaction may be 37° C., 40° C., or 50° C. In some embodiments, the reaction temperature of the in vitro transcription reaction may be 37° C. In some embodiments, the reaction time of the in vitro transcription reaction may be 0.5 h-8 h. In some embodiments, the reaction time of the in vitro transcription reaction may be 0.5 h-4 h. In some embodiments, the reaction time of the in vitro transcription reaction may be 0.5 h, 1 h, 3 h, 6 h, 8 h, or 12 h. In some embodiments, the reaction time of the in vitro transcription reaction may be 2.5 h.

In some embodiments, the reaction temperature of the in vitro transcription reaction may not be constant. For example, the in vitro transcription reaction may be performed for a first time under a first temperature, and then be performed for a second time under a second temperature to obtain reaction products of the in vitro transcription reaction. In some embodiments, the first temperature may be 30° C.-40° C., and the second temperature can be 40° C.-50° C. In some embodiments, the first temperature may be 37° C.±2° C., and the second temperature may be 50° C.±2° C. In some embodiments, the first time may be 0.5 h-5 h, and the second time may be 0.1 h-1 h. In some embodiments, the first time may be 2 h, and the second time is may be 20 min.

In some embodiments, the in vitro transcription reaction may include: making a mixture in an in vitro transcription system to obtain a mixed mixture; and conducting the in vitro transcription reaction of the mixed mixture at 37° C.±2° C. for 2 h to obtain a reaction product.

In some embodiments, the in vitro transcription reaction may include: making a mixture in an in vitro transcription system to obtain a mixed mixture; conducting the in vitro transcription reaction of the mixed mixture at 37° C.±2° C. for 2 h, and further conducting the in vitro transcription reaction of the mixed mixture at 50° C.±2° C. for 20 min to obtain the reaction product.

In some embodiments, the mixture may include nucleotides including ATP, CTP, GTP, and UTP, the DNA molecule, a buffer, T7 RNA polymerase, and nuclease-free water.

In some embodiments, the method may further include treating the reaction product with DNase I enzyme at 37° C.±2° C. for 15 minutes, and followed by an incubation step at 50° C.±2° C. for 20 min to remove the DNA molecule.

In some embodiments, the in vitro transcription reaction may include: making a mixture in an in vitro transcription system to obtain a mixed mixture; conducting the in vitro transcription reaction of the mixed mixture at 37° C.±2° C. for 2 h, treating the reaction product with DNase I enzyme at 37° C.±° C. for 15 minutes to remove the DNA molecule, and further conducting the in vitro transcription reaction of the mixed mixture at 50° C.±2° C. for 20 min to obtain the reaction product.

In some embodiments, the buffer may include Tris-HCl, $MgCl_2$, DTT, spermidine, and a concentration of $Mg^{2+}$ may be at least 32 mM.

In some embodiments, the DNA molecule may further include a poly X fragment before the full-length intron fragment, and the X may be one or two of A, C, G, T, and U. The poly X fragment may include at least 7 identical consecutive bases.

In some embodiments, the method may further include obtaining purified circular RNA by using oligo dX affinity beads. Oligo dT affinity beads may be used when the poly X fragment is poly A; oligo dA affinity beads may be used when the poly X fragment is poly T; oligo dG affinity beads may be used when the poly X fragment may be poly C; and oligo dC affinity beads may be used when the poly X fragment is poly G; and an oligo dA affinity beads may be used when the poly X fragment is poly U.

In some embodiments, the poly X fragment may include 14-40 identical consecutive bases. In some embodiments, the poly X fragment may include 14-20 identical consecutive bases. In some embodiments, the poly X fragment may include 20-29 identical consecutive bases. In some embodiments, the poly X fragment may include 14, 20, 25, 29, 31, 35, or 39 identical consecutive bases. In some embodiments, the poly X fragment may include 39 identical consecutive bases.

As circular RNAs generated in the one-step circularization do not include the poly X fragment, so the circular RNAs will not be adsorbed by the oligo dX affinity beads, while the linear RNA or other RNA fragments containing poly X in the reaction product can be enriched in the oligo dX affinity beads by affinity adsorption.

In the embodiments of the present disclosure, the circular RNA may be separated from the reaction product through the principle of affinity adsorption since sequences of poly X fragments and their corresponding complementary sequences of oligo dX have high affinity. In this process, the oligo dX affinity beads may bind to the linear RNA or other RNA fragments including the poly X fragment. Then, a magnetic field may be used to separate the affinity beads binding with the linear RNA or other RNA fragments including poly X fragment, thereby obtaining the purified circular RNA. In some embodiments, an oligo dT affinity beads may be used when the poly X fragment is poly A; an oligo dA affinity beads is used when the poly X fragment is poly T; an oligo dG affinity beads may be used when the poly X fragment is poly C; an oligo dC affinity beads may be used when the poly X fragment is poly G.

In some embodiments, the method may further include adding DNase I enzyme to a reaction product of the in vitro transcription reaction to remove the DNA molecule; adding a chelating agent to the reaction product to remove $Mg^{2+}$;

and adding RNase R to the reaction product to digest the linear RNA, thus to further purify the circular RNA in the reaction product.

In some embodiments, the chelating agent may include EDTA or other chelating agents with a function of chelating $Mg^{2+}$. In some embodiments, an amount of the chelating agent added to the reaction product may be 30-10 mM. In some embodiments, the amount of the chelating agent added to the reaction product may be 30 mM, 20 mM, or 10 mM.

In some embodiments, an amount of the RNase R added to the reaction product may be 10 U-30 U. In some embodiments, the amount of the RNase R added to the reaction product may be 10 U, 20 U, or 30 U.

Embodiments of the present disclosure provide a method for producing a target peptide by translation. In some embodiments, the method may include: obtaining the circular RNA based on the method mentioned above; transfecting a cell with the circular RNA; and starting a translation reaction in the transfected cell based on the circular RNA to produce a target peptide.

The following descriptions provide a clear and complete description for the technical solution of the present disclosure in conjunction with the embodiments. Obviously, the described embodiments are merely a portion of the embodiments of the present disclosure, not all of them. Some of these embodiments may also be replaced or combined with corresponding content in other embodiments to form new embodiments. Based on the embodiments in the present disclosure, all other embodiments obtained by those of ordinary skill in the art without creative labor conditions fall within the scope of protection of the present invention. The experimental methods in the following embodiments, unless otherwise specified, are all conventional methods. The experimental materials used in the following embodiments, unless otherwise specified, are all purchased from conventional biochemical reagent companies. The quantitative tests in the following examples are all set with three repetition experiments, and the results are averaged. It should be understood that the following embodiments are intended to better explain the present disclosure and may not be intended to limit the scope of the present disclosure.

EXAMPLES

Example 1: A DNA Molecule (e.g. a Vector) for Making a Circular RNA

As shown in FIG. 1, A represents a DNA molecule (e.g. a vector) including a homology arm, and B represents a DNA molecule (e.g. a vector) not including a homology arm. This example took a pre-tRNA$_{Leu}$ gene of genus *Anabaena* as an example to design an intron fragment, an E2 fragment and an E1 fragment, but the present disclosure was not limited to the pre-tRNA$_{Leu}$ gene of genus *Anabaena*, and other intron fragments, E2 fragments and E1 fragments from the same gene may be also used.

The DNA molecule A or the vector A included elements operably connected and arranged, from left to right, in the following order: an intron fragment (the intron fragment in this example was an intron fragment of the pre-tRNA$_{Leu}$ gene of genus *Anabaena*, and the intron fragment had the nucleotide sequence shown in SEQ ID NO. 1), an E2 fragment (the E2 fragment in this example was an exon sequence downstream of an intron of the pre-tRNA$_{Leu}$ gene of genus *Anabaena*), a 5' homology arm (the 5' homology arm sequence in this example was a sequence shown in SEQ ID NO. 12), a 3' homology arm (the 3' homology arm sequence in this example was a sequence shown in SEQ ID NO. 13), an E1 fragment (the E1 fragment in this example was an exon sequence upstream of the intron fragment of the pre-tRNA$_{Leu}$ gene of genus *Anabaena*). Based on exon sequences with lengths of 15 nt, 10 nt, 6 nt, 4 nt and 2 nt (nucleotide sequences were shown in SEQ ID NO. 8-9, and sequences GGACTT, ACTT and TT, respectively), five E1 fragments with different sizes were designed as shown in FIG. 13. Based on exon sequences with lengths of 51 nt, 40 nt, 30 nt, 20 nt, 8 nt, 6 nt, 4 nt, and 2 nt (nucleotide sequences were shown in SEQ ID NO. 2-5, and sequences AAAATCCG, AAAATC, AAAA, AA, respectively), eight E2 fragments with different sizes were designed as shown in FIG. 9.

After inserting a target gene (also known as a GOI) sequence that needs to be circularized into the circular RNA through genetic engineering techniques between the 5' homology arm sequence and 3' homology arm sequence of the vector A, or between the E2 fragment and the E1 fragment of the vector B, a DNA molecule (e.g. a vector) could be constructed under the presence of a promoter.

Figure 2:
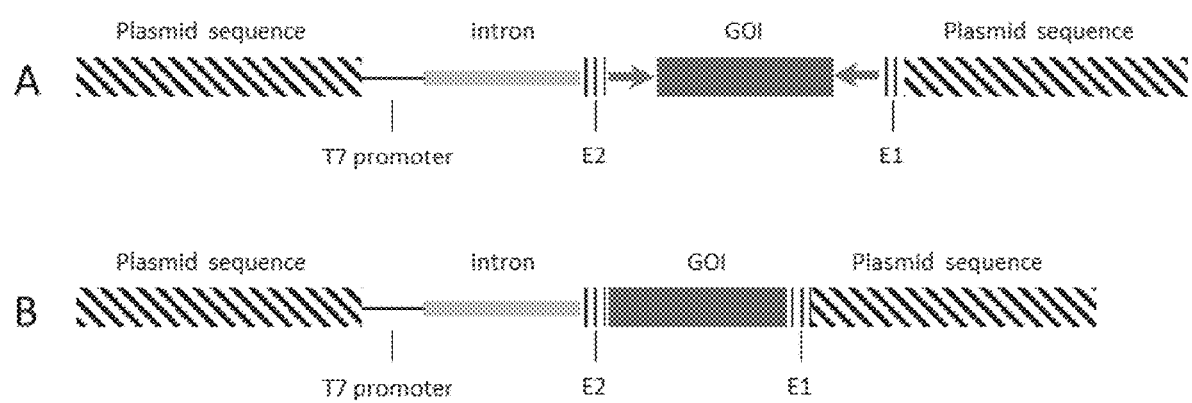
FIG. 2 is a pattern diagram illustrating an exemplary circular RNA vector including a DNA molecule that can make a circular RNA in an in vitro transcription reaction according to some embodiments of the present disclosure, wherein A in FIG. 2 is a pattern diagram including a homology arm sequence, and B in FIG. 2 is a pattern diagram not including a homology arm sequence.

In this example, the GOI fragment (the nucleotide sequence of the GOI as shown in SEQ ID NO. 6 or 7) was used as the target gene sequence that needs to be circularized into the circular RNA to prepare the DNA molecule (e.g. vector) of the circular RNA. As shown in FIG. 2, A was a vector including a homology arm, and B was a vector not including a homology arm.

Example 2: Preparing the Circular RNA

1. Preparing a Vector

In this example, a non-ligase dependent single fragment rapid cloning kit produced by Vazyme Biotech Co., Ltd was used to synthesize a DNA molecule (e.g. a vector) that can be used in an in vitro transcription reaction to prepare the circular RNA. To prepare different circular RNAs, a way of gene synthesis was used to synthesize the GOI fragment.

2. Preparing an In Vitro Transcription Template

The in vitro transcription template consisted of an intron fragment, an E2 fragment, a 5' homology arm sequence, a GOI fragment, a 3' homology arm sequence, an E1 fragment, or an intron fragment, an E2 fragment, a GOI fragment, an E1 fragment. The in vitro transcription template may be directly synthesized, obtained by constructing a plasmid for PCR amplifications, or may be obtained by cutting the plasmid using a restriction endonuclease.

In this example, PCR amplification or restriction endonuclease cleavage were used to obtain high-quality in vitro transcription templates, respectively.

Figure 3:
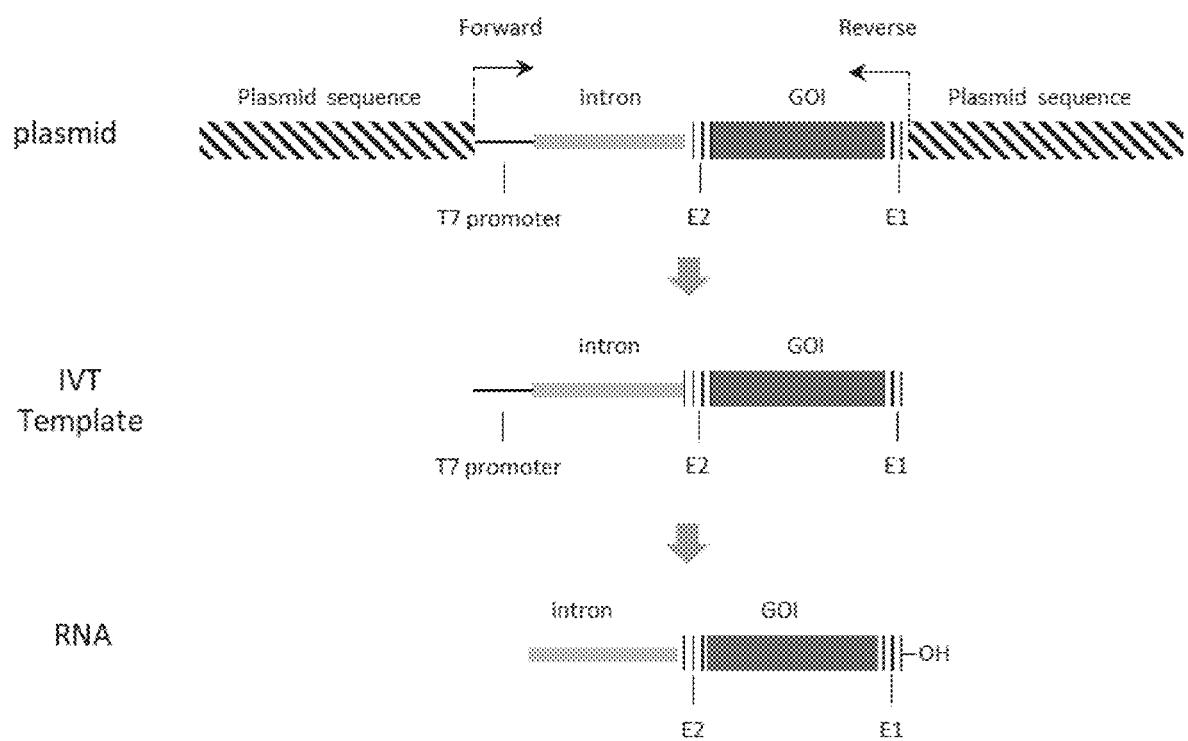
FIG. 3 is a schematic diagram illustrating an exemplary process for obtaining a DNA molecule by PCR amplifications according to some embodiments of the present disclosure.

The process for obtaining the in vitro transcription template with PCR amplifications is shown in FIG. 3. The entrusted company imported a DNA molecule including an intron fragment, an E2 fragment, a 5' homology arm sequence, a GOI fragment, a 3' homology arm sequence, an E1 fragment; or an intron fragment, an E2 fragment, a GOI fragment, an E1 fragment into a plasmid skeleton including a promoter (a plasmid skeleton including a T7 promoter was used in this example, but the plasmid skeleton is not limited to the T7 promoter, and other promoters that can initiate transcription may be used) to obtain a recombinant plasmid. A forward primer was designed before the T7 promoter sequence, and a reverse primer was accurately designed at an end of the nucleotide sequence of the E1 fragment. The PCR amplifications were performed with the recombinant plasmid as a template to obtain the in vitro transcription template. The forward primer used in this example was PCR-F: GGCCAGTGAATTGTTAATACG (SEQ ID NO. 16), and the reverse primer used in this example was PCR-R: AACTCCGTAGCGTCTCGCCG (SEQ ID NO. 17).

The reaction system was shown as below:

| PCR-F | 0.5 μL |
|---|---|
| PCR-R | 0.5 μL |
| vector | 0.1 μg |
| 2× Takara primeSTAR | 10 μL |
| RNase-free water | to 20 μL |

The reaction conditions were shown as below:

| 98° C. | 10 min | |
|---|---|---|
| 98° C. | 30 s | |
| 58° C. | 30 s | |
| 72° C. | 30 s | 35 cycles |
| 72° C. | 10 min | |
| 4° C. | ∞ | |

A DNA gel was used to recover the PCR products. A DNA agarose gel with a concentration of 2% was provided. 120V electrophoresis was performed for at least 30 min. The Omega gel recovery kit was used to recover the PCR products, RNase free water with an amount of 30 μL was added to elute the template, and a concentration of the template was determined.

Figure 4:
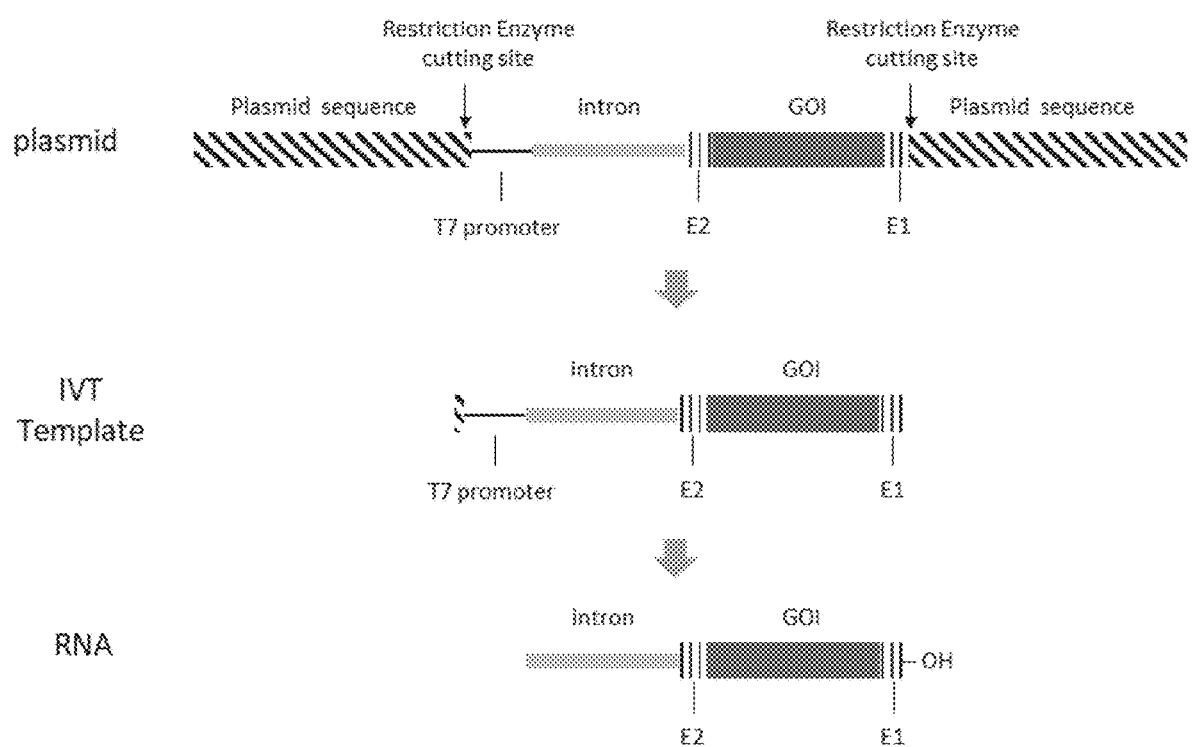
FIG. 4 is a schematic diagram illustrating an exemplary process for obtaining a DNA molecule based on a restriction endonuclease according to some embodiments of the present disclosure.

The process for obtaining the in vitro transcription template using the restriction endonuclease method is shown in FIG. 4. The entrusted company imported a DNA molecule composed of a intron fragment, an E2 fragment, a 5' homology arm sequence, a GOI fragment, a 3' homology arm sequence, an E1 fragment; or a intron fragment, an E2 fragment, a GOI fragment, an E1 fragment into a plasmid skeleton including a promoter (a plasmid skeleton including a T7 promoter was used in this example, but the plasmid skeleton may not be limited to the T7 promoter, and other promoters that can initiate transcription may be used) to obtain a recombinant plasmid. The type IIS restriction endonuclease (e.g., BspQ I) or the type II blunt restriction endonuclease (e.g., Hpa I) was used to cleave the vector, the selected restriction endonuclease site was a site at an end sequence of the E1 fragment. After enzymatic cleavage, an end of the in vitro transcription template was an exact end of the E1 fragment. The reaction conditions were shown as below:

| RNase-free water | to 20 μL |
|---|---|
| Plasmid | 10 μg |
| BspQ I (or Hpa I) | 2 μL |
| 10× reaction buffer | 2 μL |
| A total volume | 20 μL |

After uniform mixing, reacting in a water bath at 50° C. (or 37° C.) for 1 h.

A DNA gel was used to recover the PCR products. A DNA agarose gel with a concentration of 2% was provided. 120V electrophoresis was performed for at least 30 min. The Omega gel recovery kit was used to recover the PCR products, RNase free water with an amount of 30 μL was added to elute the template, and a concentration of the template was determined.

Figure 5:
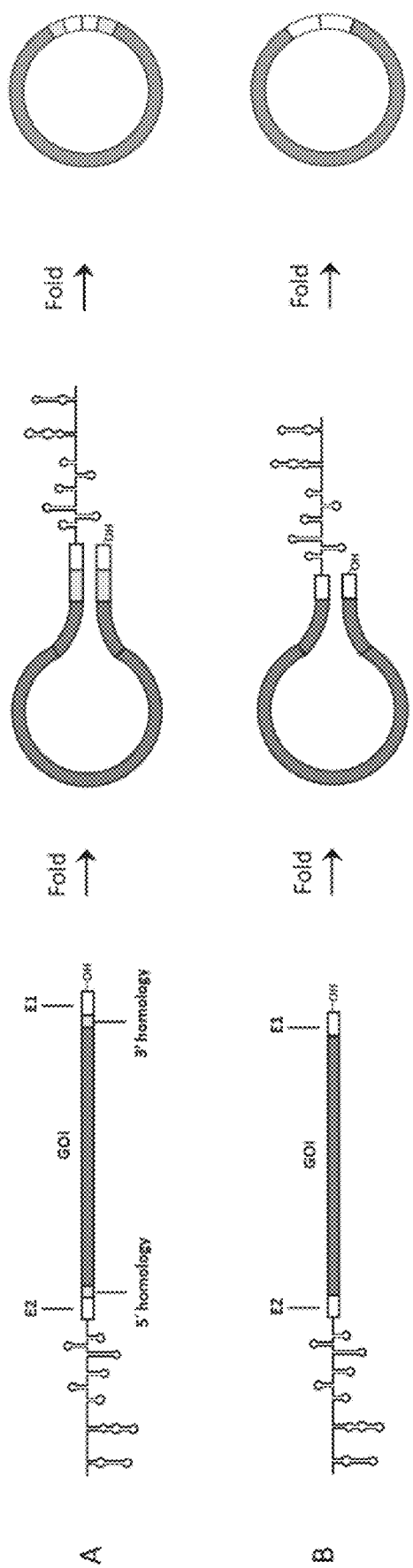
FIG. 5 is a schematic diagram illustrating an exemplary model for making a circular RNA based on a DNA molecule according to some embodiments of the present disclosure.

3. An In Vitro Transcription Reaction 3.1 A Principle of Obtaining a Stable Circular RNA in the In Vitro Transcription Reaction As shown in FIG. 5, under the action of RNA polymerase (the T7 promoter corresponding to a T7 RNA polymerase), a linear RNA sequence (RNA-OH) with a free hydroxyl group at the end of the E1 fragment was obtained by reacting with the in vitro transcription template obtained in step 2.) as the substrate. At the same time, the linear RNA itself formed a stable secondary structure, and the free hydroxyl group (U-OH) at the end of the RNA attacked a combination region of the intron fragment and the E2 fragment for a one-step transesterification reaction. Thus, an end of the E2 fragment and an end of the E1 fragment were connected together to form the stable circular RNA.

3.2 Method (1) An In Vitro Transcription Reaction

The in vitro transcription template obtained in step 2.) was used as the substrate to perform the in vitro transcription reaction with the RNA transcriptase kit (a T7 RNA transcriptase kit), thus to generate a mixture (including linear RNA and circular RNA), of which the circular RNA is as the main component.

Reaction conditions for each tube:

| ATP/CTP/GTP/UTP mix | 8 μL |
|---|---|
| the in vitro transcription template | 1 μg |
| 10× Reaction Buffer | 2 μL |
| T7 Enzyme Mix | 2 μL |
| RNase-free water | to 20 μL |

The above substances were mixed evenly, and then the in vitro transcription reaction was performed at 37° C.

(2) Digestion with DNase I Enzyme

The reaction products of the in vitro transcription reaction were treated with the DNase I enzyme for 15 minutes, to remove the DNA template. Reaction conditions for each tube were: adding 1 μL DNase I enzyme (1 U/μL) to a centrifuge tube in step (1), and mixing the DNase I enzyme with the reaction products evenly, and then reacting at 37° C. for 15 min.

(3) Recovery of RNA Molecule

The RNA molecule was purified by using a column purification kit, the concentration of the purified RNA molecule was measured.

(4) Verification with a Gel Electrophoresis

The DNA agarose gel electrophoresis was used to verify a size and an integrity of a long-fragment RNA. Specifically, 2% agarose gel was provided, and the electrophoresis was conducted at 120 V on 1 μg RNA molecule for 45 min, thus a stripe size of the RNA molecule was confirmed with the gel imaging system (results are shown in FIG. 10, FIG. 14, FIG. 17, and FIG. 20).

Figure 7:
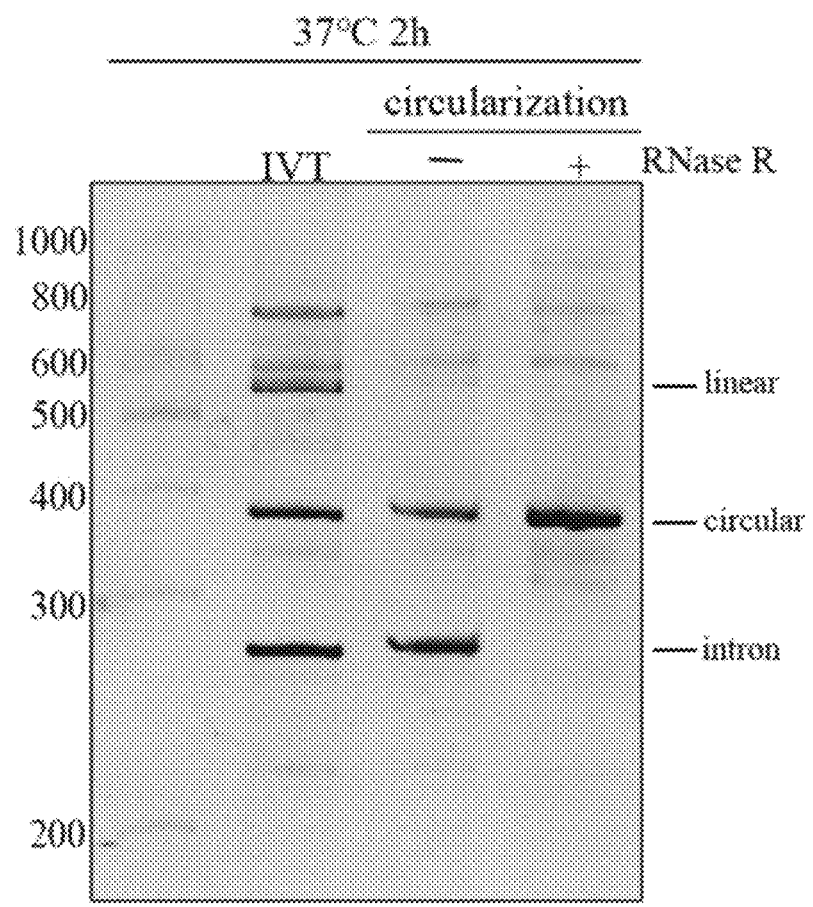
FIG. 7 shows an exemplary identification result of reaction products in an in vitro transcription reaction according to some embodiments of the present disclosure, wherein a gene of interest (GOI) fragment of a DNA molecule has a nucleotide sequence shown in SEQ ID NO. 6.
Figure 8:
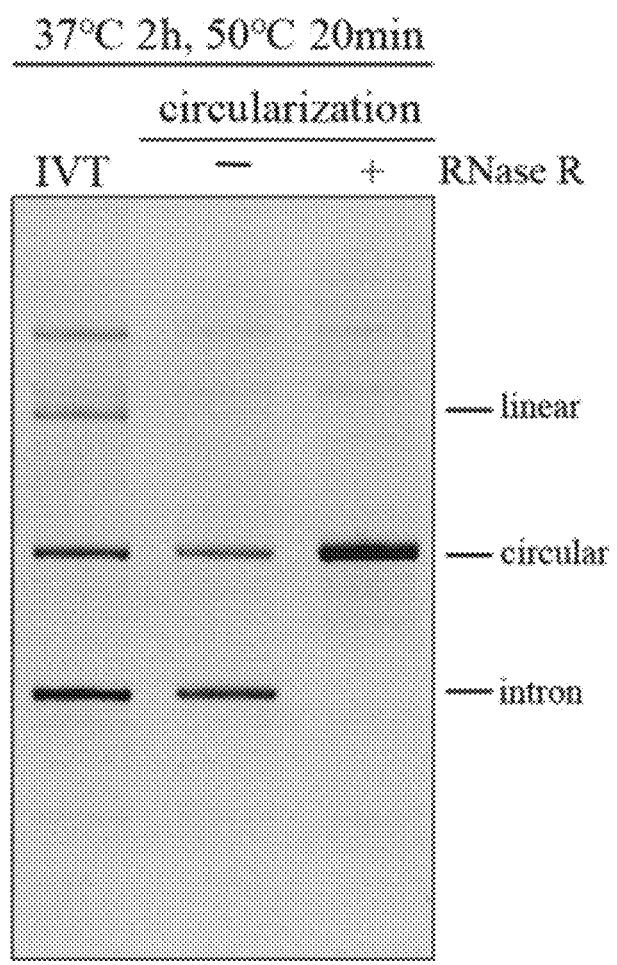
FIG. 8 shows an exemplary identification result of reaction products in an in vitro transcription reaction with optimized in vitro transcription conditions according to some embodiments of the present disclosure, wherein a GOI fragment of a DNA molecule has a nucleotide sequence shown in SEQ ID NO. 6.

The denaturing urea polyacrylamide gel electrophoresis was used to verify a size and an integrity of a long-fragment RNA. Specifically, 5% PAGE gel was provided, and the electrophoresis was conducted at 120 V on 400 ng RNA molecule for 1 h, thus a stripe size of the RNA molecule was confirmed with the gel imaging system (results are shown in FIG. 7, and FIG. 8).

The composition of the DNA molecule or the vector involved in this example is shown in Table 1

TABLE 1

The composition of the DNA molecule or the vector and corresponding transcription conditions

| Serial Number | Intron fragment | E2 | 5'-homology | GOI | 3'-homology | E1 | Transcription conditions |
|---|---|---|---|---|---|---|---|
| 1 | Yes | 51 nt | Yes | Yes | Yes | 15 nt | 37° C., 2 h |
| 2 | Yes | 51 nt | Yes | Yes | Yes | 15 nt | 37° C., 2 h |
| 3 | Yes | 51 nt | Yes | Yes | Yes | 15 nt | 37° C., 2 h; 50° C., 20 min |
| 4 | Yes | 40 nt | Yes | Yes | Yes | 15 nt | 37° C., 2 h |
| 5 | Yes | 40 nt | Yes | Yes | Yes | 15 nt | 37° C., 2 h; 50° C., 20 min |
| 6 | Yes | 30 nt | Yes | Yes | Yes | 15 nt | 37° C., 2 h |
| 7 | Yes | 30 nt | Yes | Yes | Yes | 15 nt | 37° C., 2 h; 50° C., 20 min |
| 8 | Yes | 20 nt | Yes | Yes | Yes | 15 nt | 37° C., 2 h |
| 9 | Yes | 20 nt | Yes | Yes | Yes | 15 nt | 37° C., 2 h; 50° C., 20 min |
| 10 | Yes | 8 nt | Yes | Yes | Yes | 15 nt | 37° C., 2 h |
| 11 | Yes | 8 nt | Yes | Yes | Yes | 15 nt | 37° C., 2 h; 50° C., 20 min |
| 12 | Yes | 6 nt | Yes | Yes | Yes | 15 nt | 37° C., 2 h |
| 13 | Yes | 6 nt | Yes | Yes | Yes | 15 nt | 37° C., 2 h; 50° C., 20 min |
| 14 | Yes | 4 nt | Yes | Yes | Yes | 15 nt | 37° C., 2 h |
| 15 | Yes | 4 nt | Yes | Yes | Yes | 15 nt | 37° C., 2 h; 50° C., 20 min |
| 16 | Yes | 2 nt | Yes | Yes | Yes | 15 nt | 37° C., 2 h |
| 17 | Yes | 2 nt | Yes | Yes | Yes | 15 nt | 37° C., 2 h; 50° C., 20 min |
| 18 | Yes | 8 nt | Yes | Yes | Yes | 10 nt | 37° C., 2 h |
| 19 | Yes | 8 nt | Yes | Yes | Yes | 10 nt | 37° C., 2 h; 50° C., 20 min |
| 20 | Yes | 8 nt | Yes | Yes | Yes | 8 nt | 37° C., 2 h |
| 21 | Yes | 8 nt | Yes | Yes | Yes | 8 nt | 37° C., 2 h; 50° C., 20 min |
| 22 | Yes | 8 nt | Yes | Yes | Yes | 6 nt | 37° C., 2 h |
| 23 | Yes | 8 nt | Yes | Yes | Yes | 6 nt | 37° C., 2 h; 50° C., 20 min |
| 24 | Yes | 8 nt | Yes | Yes | Yes | 4 nt | 37° C., 2 h |
| 25 | Yes | 8 nt | Yes | Yes | Yes | 4 nt | 37° C., 2 h; 50° C., 20 min |
| 26 | Yes | 8 nt | Yes | Yes | Yes | 2 nt | 37° C., 2 h |
| 27 | Yes | 8 nt | Yes | Yes | Yes | 2 nt | 37° C., 2 h; 50° C., 20 min |
| 28 | Yes | 8 nt | Yes | Yes | Yes | 15 nt CTT to GTT | 37° C., 2 h; 50° C., 20 min |
| 29 | Yes | 8 nt | Yes | Yes | Yes | 15 nt CTT to TTT | 37° C., 2 h; 50° C., 20 min |
| 30 | Yes | 8 nt | No | Yes | No | 15 nt | 37° C., 2 h; 50° C., 20 min |
| 31 | Yes | 8 nt | No | Yes | No | CTT | 37° C., 2 h; 50° C., 20 min |

4. Results

Figure 6:
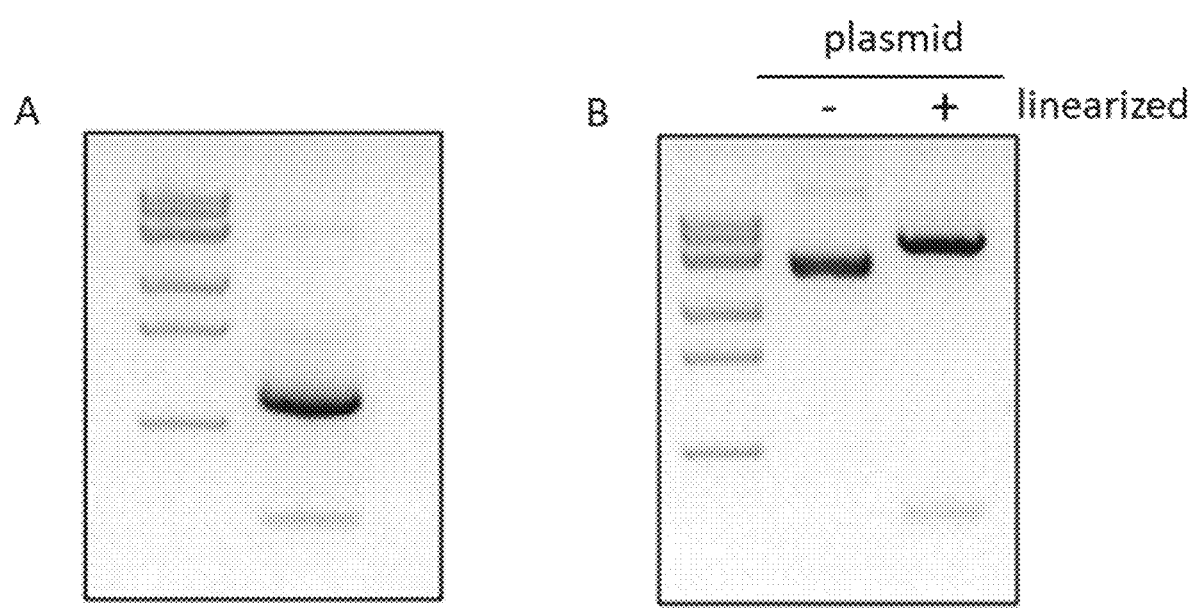
FIG. 6 shows an exemplary acquisition result of a DNA molecule, wherein A in FIG. 6 is a target band of PCR specific amplification, and B in FIG. 6 is a DNA molecule obtained based on a restriction endonuclease of Hpa l.

The acquisition result of the in vitro transcription template is shown in FIG. 6. The PCR amplifications were used to generate a sufficient amount of the circular RNA transcription templates (a result shown as A in FIG. 6, the obtained in vitro transcription template had an accurate end of the E1 fragment, while the end of the E1 fragment of the linear RNA formed by the in vitro transcription reaction was a free hydroxyl group). Alternatively, restriction endonuclease was used to cleave the plasmid including the target fragment (a result shown as B in FIG. 6, the obtained in vitro transcription template had an accurate end of the E1 fragment, and the end of the E1 fragment of the linear RNA formed by the in vitro transcription was a free hydroxyl group). The restriction endonuclease used for cleavage were type IIS restriction enzyme or type II restriction enzyme that can produce a flat end.

The template obtained based on the PCR amplifications was used for the in vitro transcription reaction, and the product generated in the in vitro transcription reaction was subjected to the circularization reaction and the digestion reaction with RNase R, respectively. The product obtained from these three reactions were identified using denaturing urea polyacrylamide gel. The identification result of the reaction product in the in vitro transcription reaction is shown in FIG. 7. In the reaction product of the in vitro transcription (IVT) reaction, the content of the circular RNA is higher compared to that of the linear RNA, indicating that most of the linear RNA undergoes circularization reaction during the in vitro transcription process.

As shown in FIGS. 7 and 8, compared with the transcription result obtained under the in vitro transcription conditions of 370 and 2 h (as shown in serial number 2 in Table 1), under the in vitro transcription conditions being 37° C., 2 h and 50° C., 20 min (as shown in serial number 3 in Table 1), the proportion of circular RNA was further increased.

Figure 10:
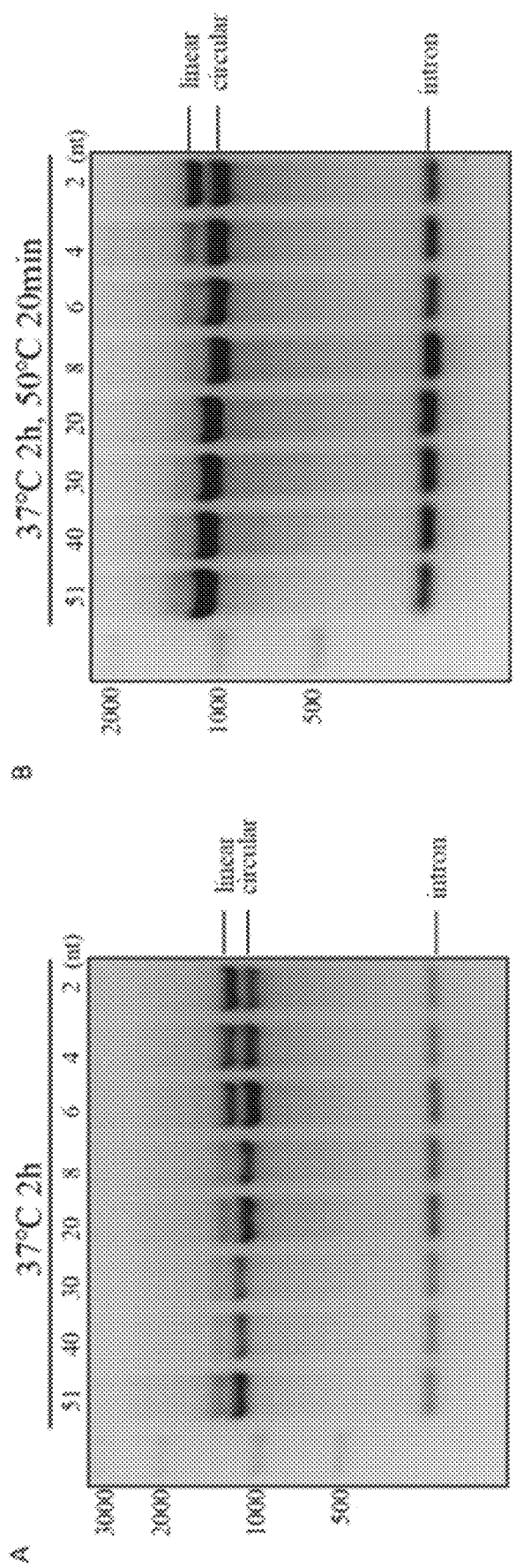
FIG. 10 shows an exemplary effect on the proportion of circular RNAs in reaction products generated in an in vitro transcription reaction by different E2 fragments with different lengths according to some embodiments of the present disclosure, wherein a GOI fragment of a DNA molecule has the nucleotide sequence shown in SEQ ID NO. 7.
Figure 11:
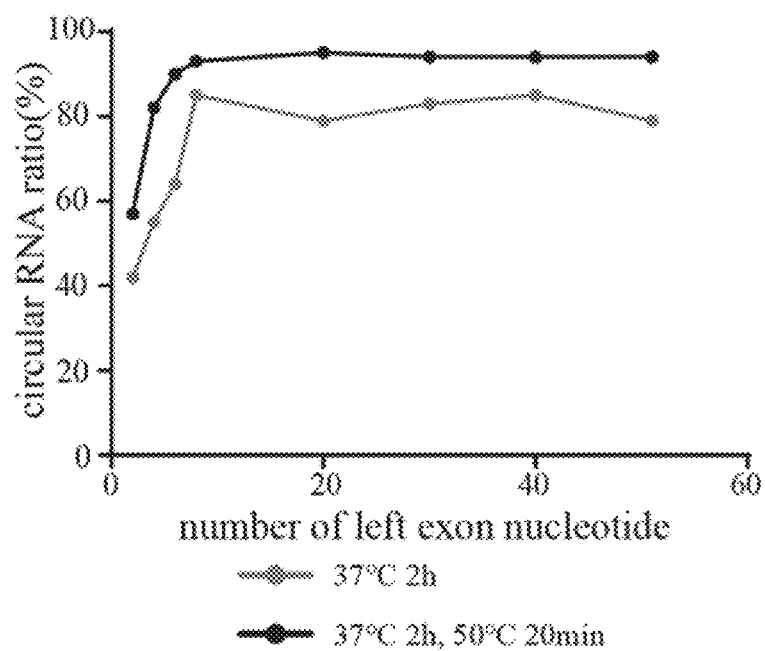
FIG. 11 shows an exemplary circular RNA quantitative result of effect on the proportion of circular RNAs in reaction products generated in an in vitro transcription reaction by different E2 fragments with different lengths according to some embodiments of the present disclosure.
Figure 12:
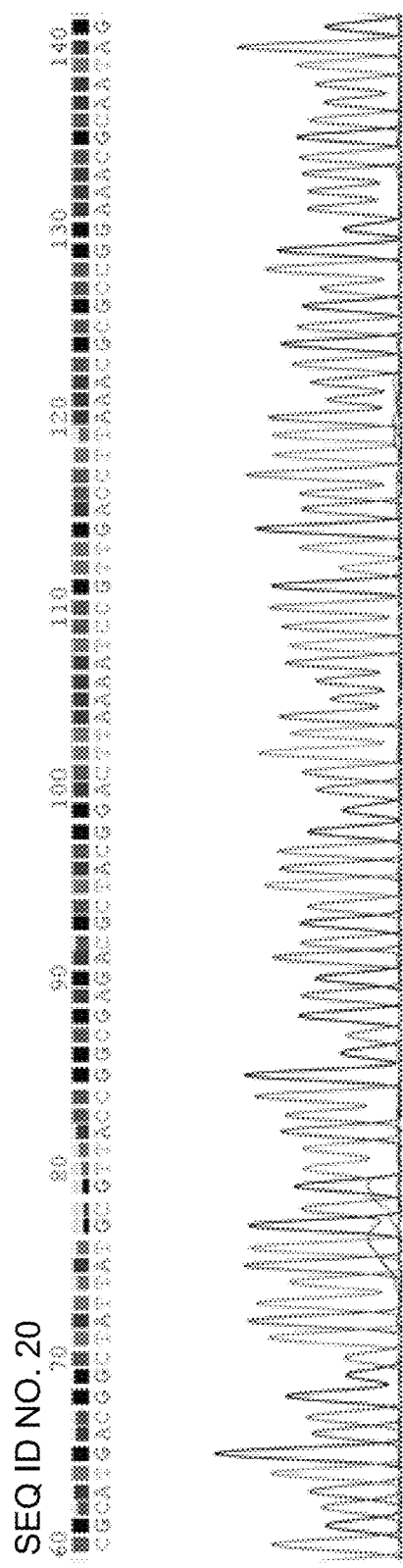
FIG. 12 shows an exemplary Sanger sequencing result of a circularization site of a circular RNA of an E2 fragment with a length of a nucleotide sequence of the circular RNA being 8 nt according to some embodiments of the present disclosure, wherein the E2 fragment is in a fragment which has the nucleotide sequence shown in SEQ ID NO. 20.

The E2 fragments with different lengths in size (as shown in FIG. 9) were reacted under normal in vitro transcription conditions (37° C., 2 h) and optimized in vitro transcription conditions (37° C., 2 h; 50° C., 20 min), which are shown in serial numbers 2-17 in Table 1, respectively, and the circular RNA ratio and linear RNA ratio in the reaction product was quantified using the software image J. The quantitative results are shown in FIGS. 10 and 11, and the length of the E2 fragment may affect the proportion of the circular RNA in the in vitro transcription reaction product. When the length of the E2 fragment is between 8-51 nt, the proportion of the circular RNA in the in vitro transcription reaction product may be about 85%-90%, that is, the proportion of the circular RNA in the in vitro transcription reaction product may not be affected. When the length of the E2 fragment is less than 8 nt, the proportion of circular RNA may be seriously affected, and the proportion of the circular RNA in the in vitro transcription reaction product may be below 80%. Using an E2 fragment including 8 bases in size included in the template to perform the in vitro transcription reaction, the reaction product was digested with RNase R, followed a RT-PCR was performed. The product of RT-PCR was connected to a T vector for Sanger sequencing, and the Sanger sequencing result is shown in FIG. 12. The Sanger sequencing result indicates that the circularization site of the circular RNA is single and accurate.

Figure 14:
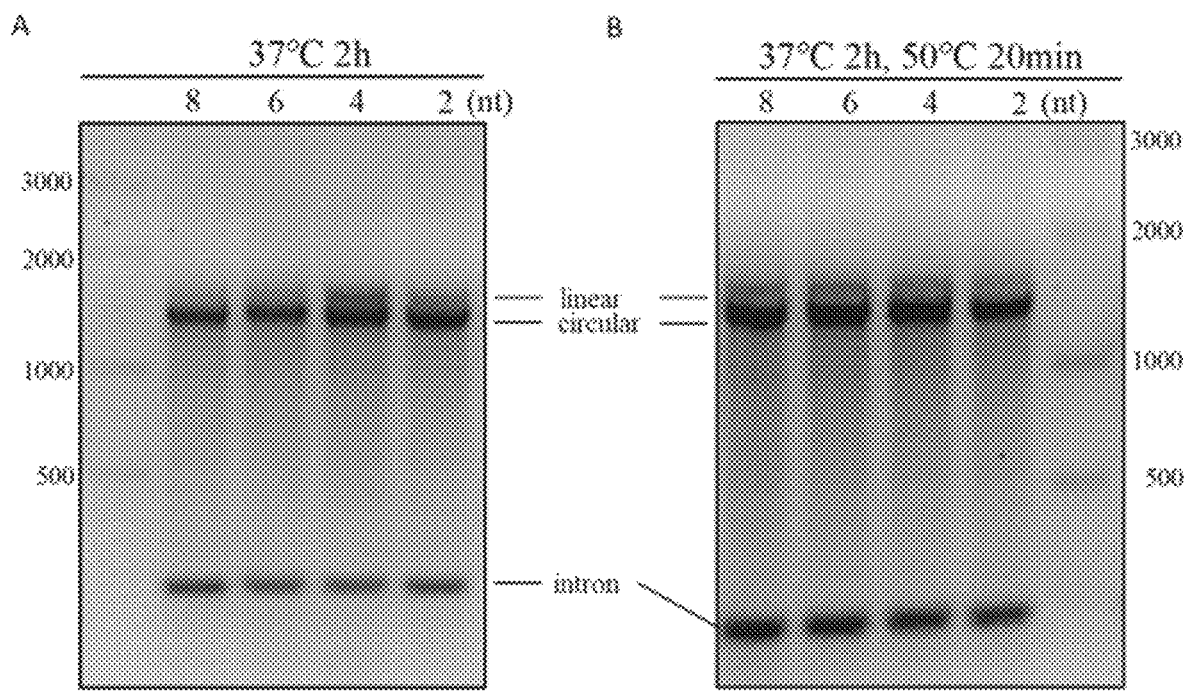
FIG. 14 shows an exemplary effect on the proportion of circular RNAs in reaction products generated in an in vitro transcription reaction by different E1 fragments with different lengths according to some embodiments of the present disclosure, wherein a GOI fragment of a DNA molecule has the nucleotide sequence shown in SEQ ID NO. 7.
Figure 15:
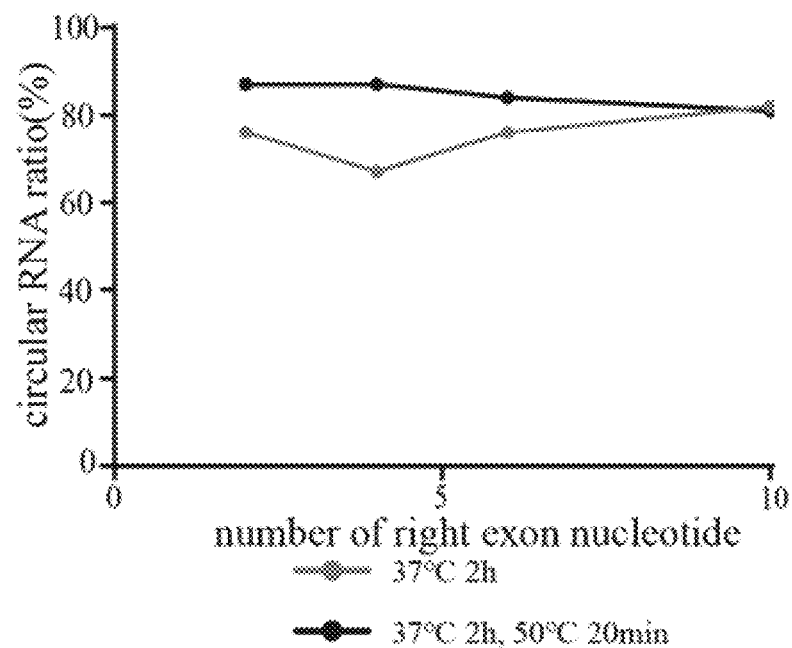
FIG. 15 shows an exemplary circular RNA quantitative result of effect on a proportion of the circular RNA in reaction products generated in an in vitro transcription reaction by different E1 fragments with different lengths according to some embodiments of the present disclosure.

Different lengths of E1 fragments (as shown in FIG. 13) were used to react under normal in vitro transcription conditions (37° C., 2 h) and optimized in vitro transcription conditions (37° C., 2 h; 50° C., 20 min), which are shown in serial numbers 10, 11, and 18-27 in Table 1, respectively, and the proportion of circular RNA and the proportion of linear RNA in the reaction product was quantified using the software image J. The quantitative results are shown in FIG. 14 and FIG. 15. Different lengths of E1 fragments were tested under normal in vitro transcription conditions (37° C., 2 h, A shown in FIG. 14) and optimized in vitro transcription conditions (37° C., 2 h; 50° C., 20 min, B shown in FIG. 14), respectively. The results show that the length of the E1 fragment has little effect on the proportion of the circular RNA in the in vitro transcription reaction.

Figure 16:
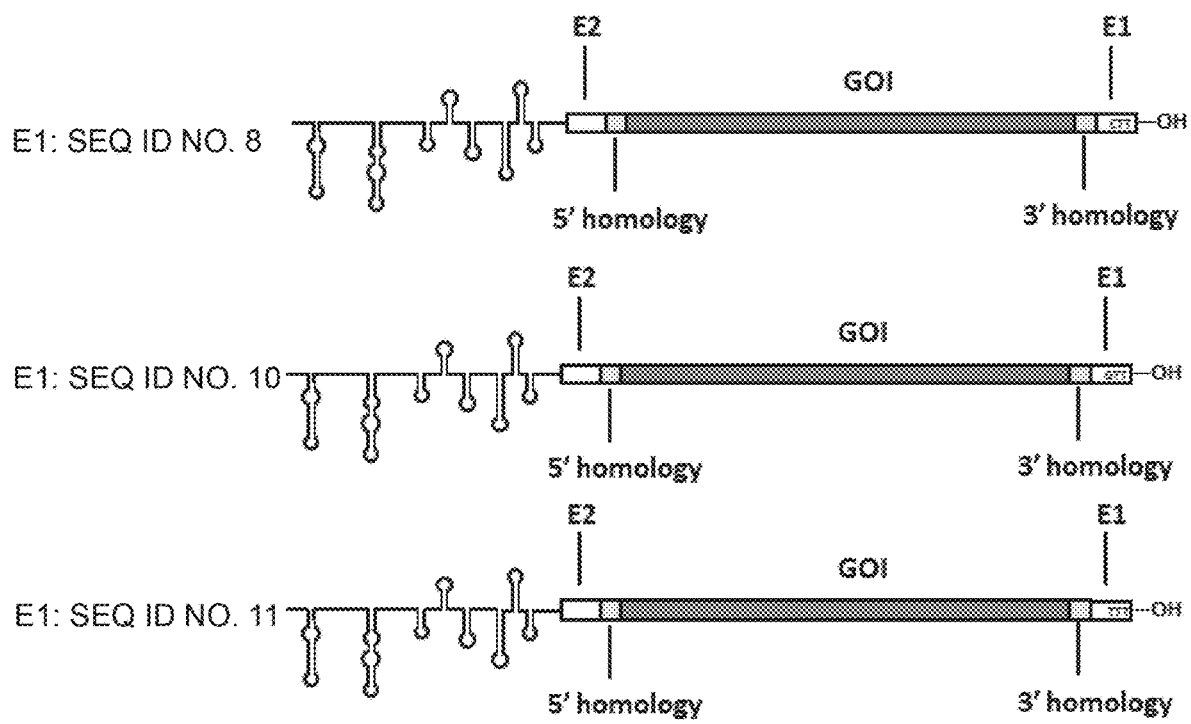
FIG. 16 is a pattern diagram illustrating a process of optimizing a sequence on 3' end of an E1 fragment (CTT on an end of the sequence mutating into GTT or TTT, respectively) according to some embodiments of the present disclosure.
Figure 17:
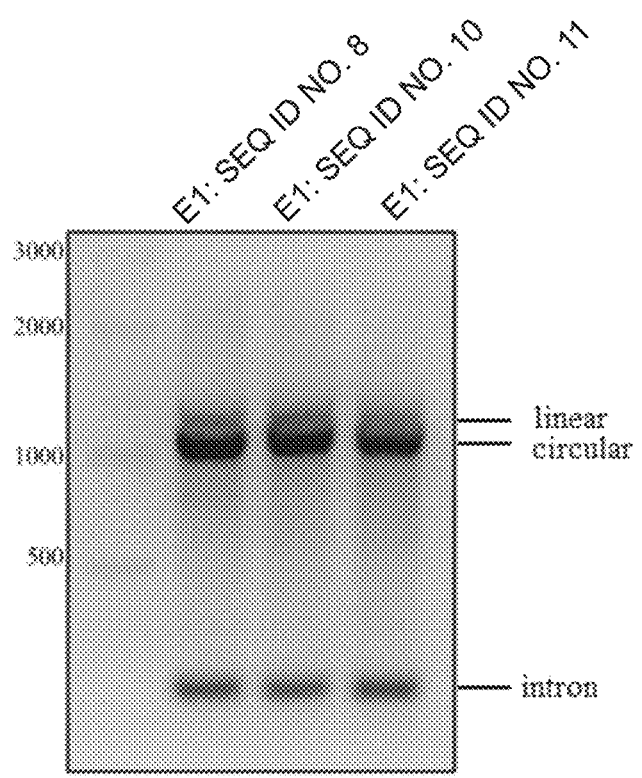
FIG. 17 shows an exemplary result of an in vitro transcription reaction (transcription conditions: 37° C., 2 h; 50° C., 20 min) using a DNA molecule including an optimized E1 fragment in FIG. 16 as a template according to some embodiments of the present disclosure.
Figure 18:
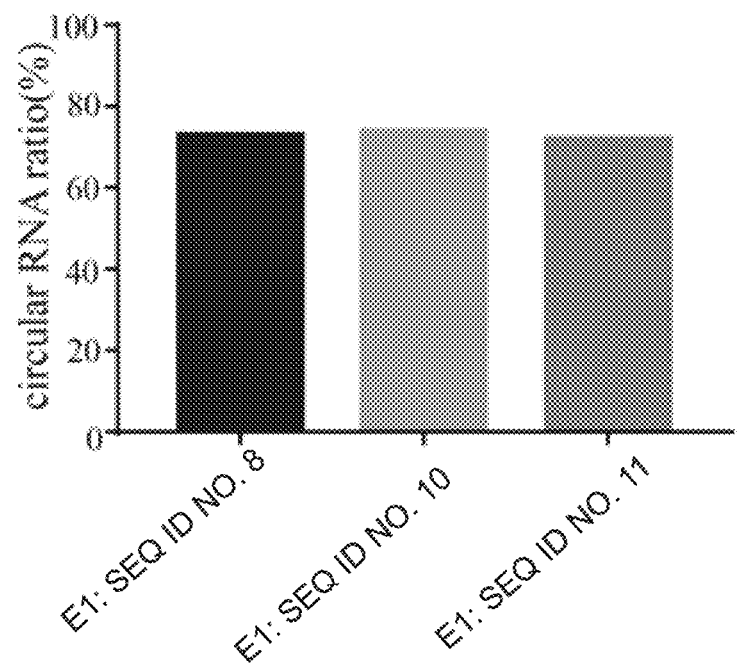
FIG. 18 shows an exemplary circular RNA quantitative result of circular RNAs of optimized E1 fragments in FIG. 16 after optimizing a sequence on 3' end according to some embodiments of the present disclosure.

After mutating the 3' end sequence of the E1 fragment with a length of 15 nt from CTT to GTT or TTT (as shown in FIG. 16), the proportion of the circular RNA in the reaction product of the in vitro transcription reaction (37° C., 2 h; 50° C., 20 min as shown in serial numbers 28-29 in Table 1) was detected (and quantified using the software image J. The quantitative results are shown in FIGS. 17 and 18, indicating that mutating the end sequence of the E1 fragment from CTT to GTT or TTT did not affect the proportion of circular RNA in the in vitro transcription reaction product.

Figure 19:
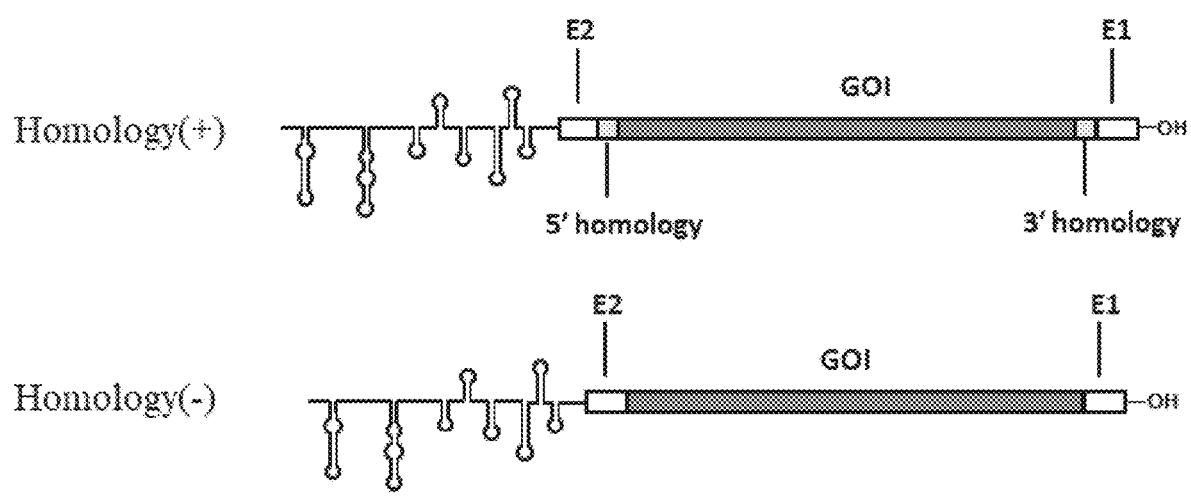
FIG. 19 is a pattern diagram illustrating a DNA molecule with or without a homology arm sequence according to some embodiments of the present disclosure.
Figure 20:
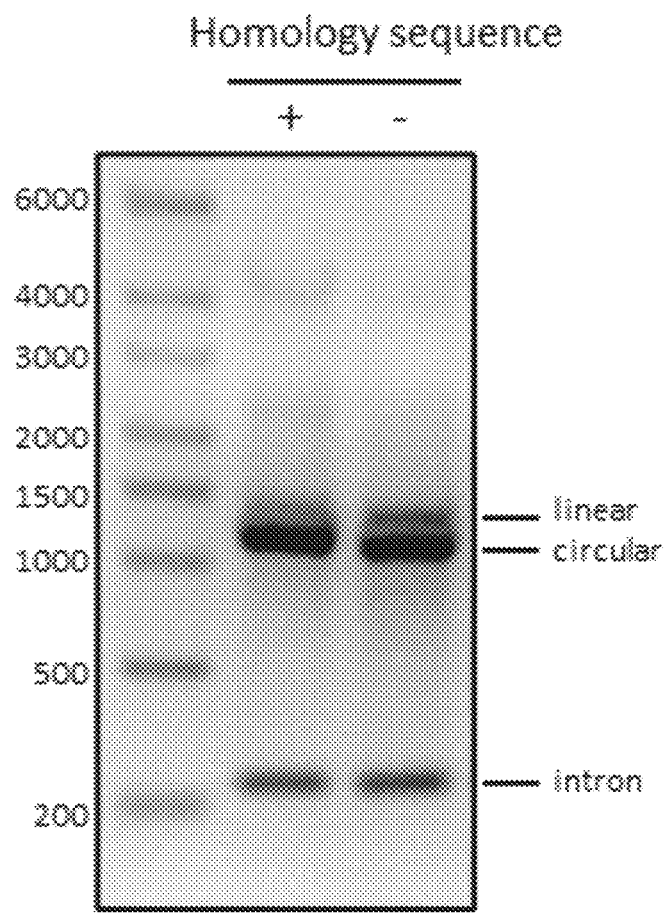
FIG. 20 shows an exemplary effect on the proportion of circular RNAs in reaction products generated in an in vitro transcription reaction by a DNA molecule with or without a homology arm sequence according to some embodiments of the present disclosure, wherein a GOI fragment of a DNA molecule has the nucleotide sequence shown in SEQ ID NO. 7.
Figure 21:
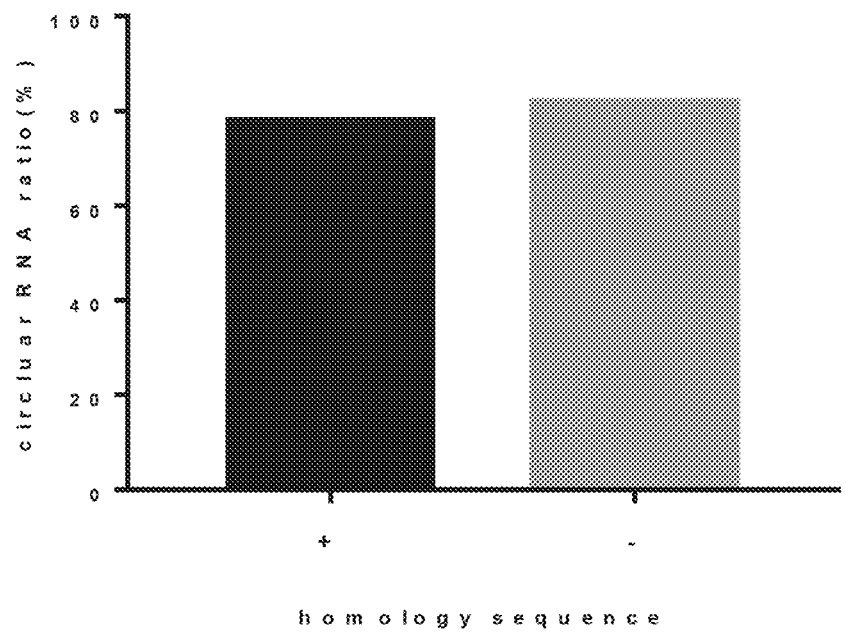
FIG. 21 shows an exemplary circular RNA quantitative result of circular RNAs obtained in FIG. 20 according to some embodiments of the present disclosure.

When the homology arm sequence (as shown in FIG. 19) is omitted, the proportion of the circular RNA in the reaction product after the in vitro transcription reaction (37° C., 2 h; 50° C., 20 min) was quantified using the software image J. The quantitative results are shown in FIGS. 20 and 21. Compared with including homology arms (homology (+)) in the sequence, as shown in serial number 11 in Table 1), removing the 5' homology arm sequence and the 3' homology arm sequence (homology (−), as shown in serial number 30 in Table 1) from the sequence did not affect the proportion of circular RNA in the reaction product, and the circularization result without the homology arm sequence is equivalent to the circularization result with the homology arm sequences, indicating that the circularization of the linear RNA is not affected. In addition, costs of preparing the DNA molecule or the vector not including a homology arm sequence can be reduced, while the introduction of other foreign genes into the circular RNA product can be avoided.

Figure 22:
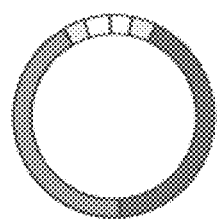
FIG. 22 is a schematic diagram illustrating an exemplary application model for making a circular RNA based on a linear RNA according to some embodiments of the present disclosure.
Figure 22:
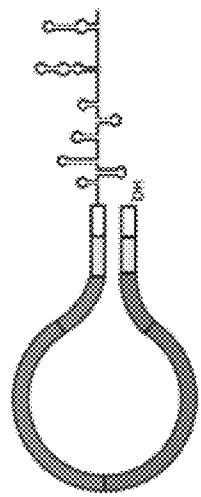
Figure 22:
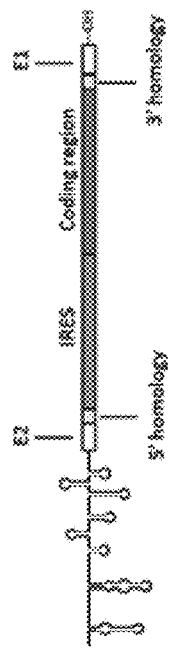

Example 3: A Method for Preparing a Vector of a Translatable Circular RNA and a Method for Translating to Produce Proteins Taking the process of translating and detecting circular RNA that can express green fluorescent protein (GFP) as an example:

The application model for making a circular RNA through a linear RNA is shown in FIG. 22. A structure of the RNA, from the 5' end to the 3' end, is in the following order: an intron fragment (the intron fragment in this example was an intron fragment of the pre-tRNA$_{Leu}$ gene of genus *Anabaena*, and the intron fragment had the nucleotide sequence shown in SEQ ID NO. 1), an E2 fragment (the E2 fragment in this example was an exon sequence AAAATCCG with a length of 8 nt downstream of an intron of the pre-tRNA$_{Leu}$ gene of genus *Anabaena*), 5' homology arm sequence (the 5' homology arm sequence in this example was a sequence shown in SEQ ID NO. 12), an IRES fragment (the IRES fragment in this example was an IRES fragment of the CVB3, and the IRES fragment had a nucleotide sequence shown in SEQ ID NO. 14), an open reading frame (ORF) (the ORF in this example was an ORF of the GFP, which had a nucleotide sequence shown in SEQ ID NO. 15) with a complete target gene that need to be expressed in cells or animals, a 3' homology arm sequence (the 3' homology arm sequence in this example was a sequence shown in SEQ ID NO. 13), an E1 fragment (the E1 fragment in this example was an exon sequence ACTT with a length of 4 nt downstream of an intron of the pre-tRNA$_{Leu}$ gene of genus *Anabaena*).

An in vitro transcription reaction: the operations of the in vitro transcription reaction in Example 3 was the same as the operation of the in vitro transcription reaction in Example 2. The circular RNA obtained in the in vitro transcription reaction was transfected into cells or animals, and ribosomes was recruited for translation under the action of IRES to obtain a target peptide.

1. Method

The purified circular RNA after being digested by RNase R was transfected into a HEK 293T cell in a 6-hole plate using a Lipofectamine MessengerMAX liposome transfection reagent: approximately 1×10$^6$ cells in a hole, 125 UL Opti-MEM was used to dilute 3.75 μL Lipofectamine MessengerMAX and 1 μg mixture of the circular RNA, respectively, and the diluted Lipofectamine MessengerMAX and diluted mixture of the circular RNA were mixed, and the mixture of the diluted Lipofectamine MessengerMAX and diluted mixture of the circular RNA was incubated at a room temperature for 15 min. Then, the incubating product was added to a cell culture medium. After 6 hours, the cell culture medium was replaced with fresh culture medium. The cells generated in the replaced culture medium were collected after 48 hours of cultivation. After removing the culture medium, and 1×PBS buffer was used to rinse the cells, 1×SDS lysate with dye was used to lyse and collect total proteins of the cells. An SDS-PAGE gel electrophoresis was performed. Specifically, 10% SDS-PAGE gel was provided, and a protein Marker and 10 μL sample was added into each of the 6 holes, and a mark was made. The electrophoresis was performed under condition with a voltage of 120V for 70 min. 0.45 μm PVDF membrane was used for transferring, and then a α-ACTB antibody and a α-GFP antibody were used for incubating, respectively. Then, a secondary antibody incubation and an ECL luminescence detection photography were performed. ACTB was used as an internal reference protein to analyze a relative expression level of the GFP to detect the produced proteins.

2. Result

Figure 23:
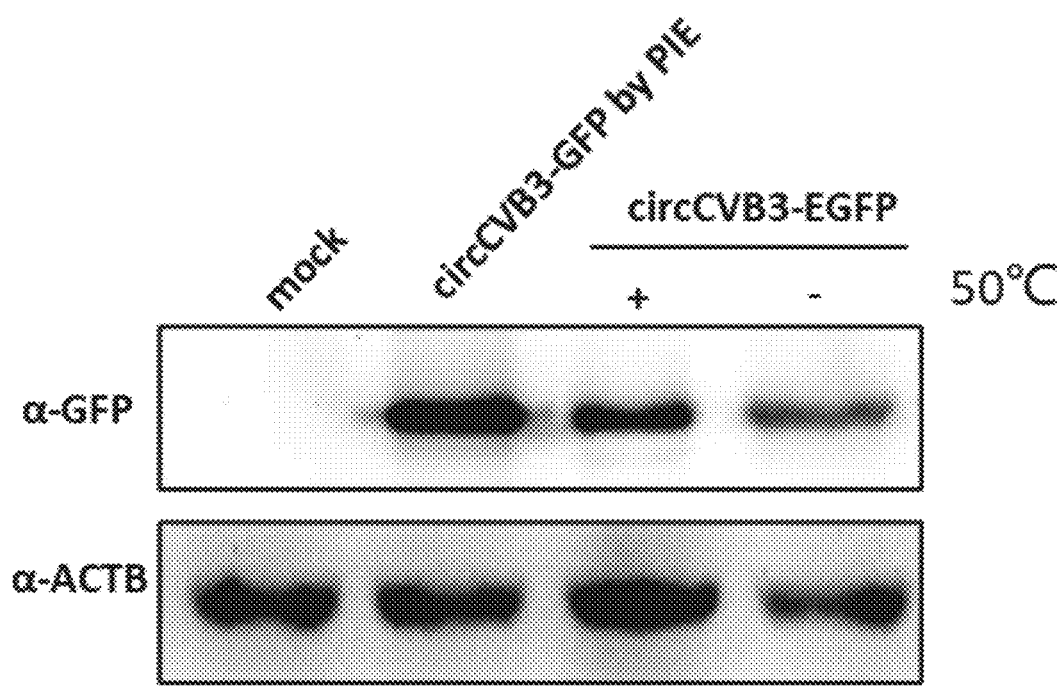
FIG. 23 shows an exemplary result of a circular RNA obtained by methods provided in the present disclosure translating and producing green fluorescent protein (GFP) in a cell according to some embodiments of the present disclosure.

GFP protein efficiency expressed by various circular RNAs carrying GFP coding sequences in HEK293T cell line was compared using protein imprinting technology. The comparison result is shown in FIG. 23. Specifically, a blank plasmid was in lane 1. A circCVB3-GFP molecule obtained through traditional PIE circularization was in lane 2. A circCVB3-GFP molecule obtained with optimized in vitro transcription conditions by digesting and purifying with RNase R based on the technology described in the present disclosure was in lane 3. A circCVB3-GFP molecule obtained with normal in vitro transcription conditions by digesting and purifying with RNase R based on the technology described in the present disclosure was in lane 4. The above four molecules were transfected into HEK293T cells using Lipo3000 for 48 h, and the cell lysate was harvested. A protein blotting was used to detect the expression of GFP. The result indicated that using the technology described in the present disclosure, the obtained circular RNA molecules can be expressed normally in cells, and can produce active proteins.

Figure 24:
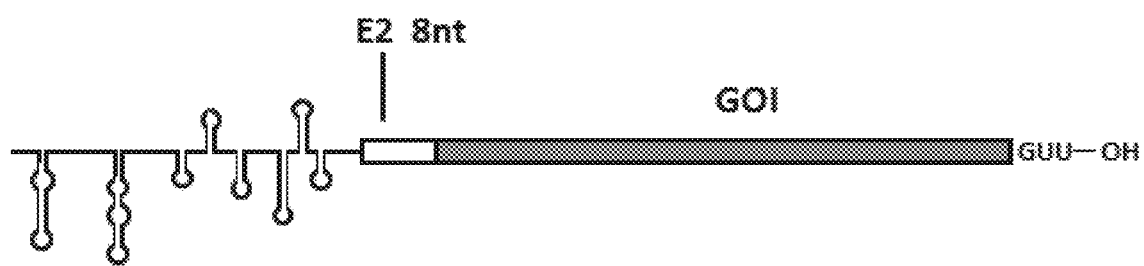
FIG. 24 is a pattern diagram illustrating a sequence of an in vitro circularization system according to some embodiments of the present disclosure.

In summary, the DNA molecule or vector for the in vitro transcription reaction to make the circular RNA in the present disclosure included elements operably connected and arranged, from left to right, in the following order: an intron fragment (the intron fragment in this example was an intron fragment of the pre-tRNA$_{Leu}$ gene of genus Anabaena, and the intron fragment had the nucleotide sequence shown in SEQ ID NO. 1), an E2 fragment (the E2 fragment in this example was an exon sequence AAAATCCG with a length of 8 nt downstream of an intron of the pre-tRNA$_{Leu}$ gene of genus Anabaena), a GOI fragment (a RNA sequence that requires to be circularized, and different sequences were selected based on different purposes of circularization), an E1 fragment (the E1 fragment in this example was an exon sequence CTT downstream of an intron of the pre-tRNA$_{Leu}$ gene of genus Anabaena). The above compositions formed a transcription template, and the linear RNA sequence formed in the in vitro transcription reaction based on a promoter is shown in FIG. 24. A free hydroxyl group was carried at the end of the E1 fragment. The linear RNA was further circularized to form the circular RNA. When a length of the RNA sequence that needs to be circularized exceeds 2000 nt, a 5' homology arm sequence was inserted after the E2 fragment, and a 3' homology arm sequence was inserted before the E1 fragment.

Figure 25:
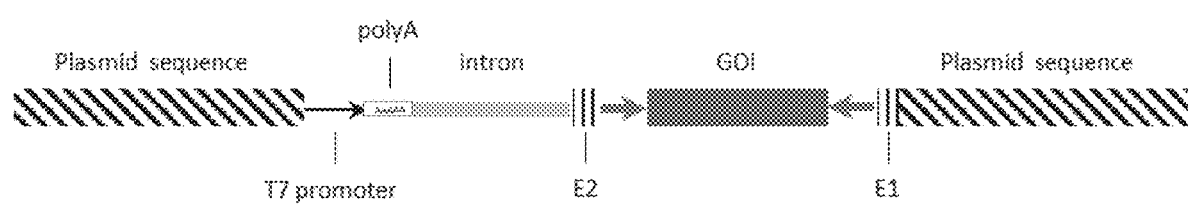
FIG. 25 is a schematic diagram illustrating an exemplary vector that has a poly A fragment according to some embodiments of the present disclosure.

Example 4: Preparing a Vector for Making a Circular RNA for Affinity Purification As shown in FIG. 25, in this example, an intron fragment, an E2 fragment, and an E1 fragment was designed using the pre-tRNA$_{Leu}$ gene of genus Anabaena, which is not limited to the pre-tRNA$_{Leu}$ gene of genus Anabaena, but an intron fragment, an E2 fragment, and an E1 fragment can be from other sources of the same gene.

A vector included elements operably connected and arranged, from left to right, in the following order: 29 consecutive A bases, an intron fragment (the intron fragment in this example was an intron fragment of the pre-tRNA$_{Leu}$ gene of genus Anabaena, and the intron fragment had the nucleotide sequence shown in SEQ ID NO. 1), an E2 fragment (the E2 fragment in this example was an exon sequence downstream of an intron of the pre-tRNA$_{Leu}$ gene of genus Anabaena, 51 nt, which had the nucleotide sequence shown in SEQ ID NO. 2), 5' homology arm sequence (the 5' homology arm sequence in this example was a sequence shown in SEQ ID NO. 12), 3' homology arm sequence (the 3' homology arm sequence in this example was a sequence shown in SEQ ID NO. 13), an E1 fragment (the E1 fragment in this example was an exon sequence upstream of the intron fragment of the pre-tRNA$_{Leu}$ gene of genus Anabaena, 15 nt, which had the nucleotide sequence shown in SEQ ID NO. 8).

After inserting a target gene sequence (shown in FIG. 25) between the 5' homology arm sequence and the 3' homology arm sequence of the vector through genetic engineering techniques, in the presence of a promoter, the constructed DNA molecule (e.g. vector) may be used as a transcription template to circularize in an in vitro transcription reaction to produce the circular RNA.

Example 5: Preparing a DNA Molecule (e.g. Vector) and a Circular RNA for Affinity Purification 1. A DNA Molecule (e.g. Vector)

Figure 26:
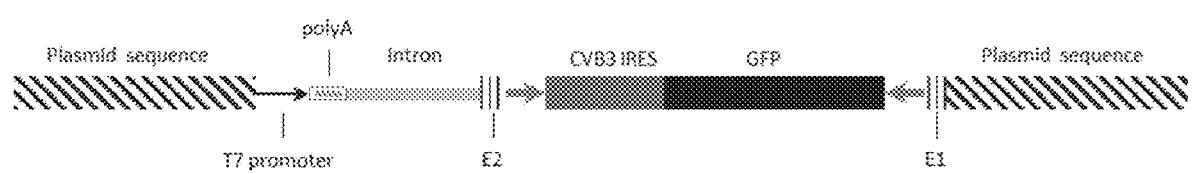
FIG. 26 is a schematic diagram illustrating an exemplary vector that has a poly A fragment and can express GFP according to some embodiments of the present disclosure.

In this example, the GFP (which had the nucleotide sequence show in SEQ ID NO. 15) was designated as a target gene sequence that needs to be circularized into an RNA to prepare a DNA molecule (e.g. vector) for making the circular RNA for affinity purification as shown in FIG. 26.

The vector included elements operably connected and arranged, from left to right, in the following order: 29 consecutive A bases, an intron fragment (the intron fragment in this example was an intron fragment of the pre-tRNA$_{Leu}$ gene of genus Anabaena, and the intron fragment had the nucleotide sequence shown in SEQ ID NO. 1), an E2 fragment (the E2 fragment in this example was an exon sequence downstream of an intron of the pre-tRNA$_{Leu}$ gene of genus Anabaena, 51 nt, which had the nucleotide sequence shown in SEQ ID NO. 2), 5' homology arm sequence (the 5' homology arm sequence in this example was a sequence shown in SEQ ID NO. 12), a CVB3 IRES sequence (the CVB3 IRES sequence in this example was a sequence shown in SEQ ID NO. 14), 3' homology arm sequence (the 3' homology arm sequence in this example was a sequence shown in SEQ ID NO. 13), an E1 fragment (the E1 fragment in this example was an exon sequence upstream of the intron fragment of the pre-tRNA$_{Leu}$ gene of genus Anabaena, 15 nt, which had the nucleotide sequence shown in SEQ ID NO. 8). In the presence of a promoter, the constructed DNA molecule (e.g. vector) was used as a transcription template to circularize in vitro to produce the circular RNA.

The preparation of the vector: on the basis of an empty vector described in this example, in order to prepare different circular RNAs, a gene synthesis method was used to synthesize the target GFP. The GFP sequence was inserted into the empty vector (in this example, a non-ligase dependent single fragment rapid cloning kit produced by Vazyme Biotech Co., Ltd was used to synthesize the vector) including the homology arms mentioned in the example to synthesize a vector that can be used for the in vitro transcription reaction to form the circular RNAs.

2. The Preparation of the In Vitro Transcription Template

The composition of the in vitro transcription template was: 29 nt consecutive A bases, an intron fragment, an E2 fragment, a 5' homology arm sequence, a CVB3 IRES sequence, a GFP sequence, a 3' homology arm sequence, an E1 fragment. The in vitro transcription template may be directly synthesized, obtained by constructing a plasmid for PCR amplifications, or obtained by cutting the plasmid using a restriction endonuclease.

In this example, the way of restriction endonuclease cleavage was used to obtain high-quality in vitro transcription template. The entrusted company imported a DNA molecule composed of 29 nt consecutive A bases, an intron fragment, an E2 fragment, a 5' homology arm sequence, a CVB3 IRES sequence, a GFP sequence, a 3' homology arm sequence, and an E1 fragment into a plasmid skeleton including a promoter (a plasmid skeleton including a T7 promoter was used in this example, but the plasmid skeleton may not be limited to the T7 promoter, and other promoters that can initiate transcription may be used) to obtain a recombinant plasmid (including the T7 promoter, 29 nt poly A, the intron fragment, the E2 fragment, the 5' homology arm sequence, the CVB3 IRES sequence, the GFP sequence, the 3' homology arm sequence, and the E1 fragment). The type IIS restriction endonuclease (e.g., BspQ I) was used to cleave the vector of the circular RNA, and the selected restriction enzyme cleavage site was a site including an end sequence of the E1 fragment. After performing the enzyme cleavage with the restriction endonuclease, the end of the in vitro transcription template was an accurate end sequence of the E1 fragment. The reaction conditions were as follows:

| | |
|---|---|
| RNase-free water | to 20 μL |
| Plasmid | 10 μg |
| BspQ I | 2 μL |
| 10× reaction buffer | 2 μL |
| A total volume | 20 μL |

After uniform mixing, reacting with water bath at 50° C. for 1 h.

A DNA gel was used to recover the enzyme cleavage products. A DNA agarose gel with a concentration of 2% was provided. 120V electrophoresis was performed for at least 30 min. The Omega gel recovery kit was used to recover the enzyme cleavage products, and RNase free water with an amount of 30 μL was added to elute the template, and a concentration of the template was determined.

3. An In Vitro Transcription Reaction
3.1. The In Vitro Transcription Reaction

The in vitro transcription template obtained in step 2.) was used as the substrate to perform the in vitro transcription reaction with the RNA transcriptase kit (a T7 RNA transcriptase kit), thus to generate a mixture (including linear RNA and circular RNA), of which the circular RNA is as the main component.

Reaction Conditions for Each Tube:

| | |
|---|---|
| ATP/CTP/GTP/UTP mix | 8 μL |
| the in vitro transcription template | 1 μg |
| 10× Reaction Buffer | 2 μL |
| T7 Enzyme Mix | 2 μL |
| RNase-free water | to 20 μL |

The above substances were mixed evenly, and then the in vitro transcription reaction was performed at 37° C. for 2 h.

3.2. Digestion with DNase I Enzyme

The reaction products of the in vitro transcription reaction were treated with the DNase I enzyme for 15 minutes, to remove the DNA template. Reaction conditions for each tube were: adding 1 μL DNase I enzyme (1 U/μL) to a centrifuge tube in step (1), and mixing the DNase I enzyme with the reaction products evenly, and then reacting at 37° C. for 15 min.

3.3 Recovery of RNA Molecule 7.5M LiCl was used to precipitate the RNA, and the RNase-free water was added to dissolve the RNA, and a concentration of the RNA was determined.

3.4 Verification with a Gel Electrophoresis

2% agarose gel was provided, and the electrophoresis was conducted at 120 V on 1 μg RNA molecule for 45 min, thus a stripe size of the RNA molecule was confirmed with the gel imaging system.

4. Optimization of the In Vitro Transcription (IVT) System

In the in vitro transcription reaction, a composition of the 10×Transcription buffer may determine an amount of the IVT products and proportions of components of the IVT products. Therefore, the optimization for 10×Transcription buffer is crucial. The main components of 10×Transcription buffer include Tris HCl, $MgCl_2$, DTT, Spermidine, etc. Among these components, a concentration of $Mg^{2+}$ directly affects the amount of the IVT products. Meanwhile, the $Mg^{2+}$ may also be directly involved in a transesterification and an RNA hydrolysis process. Therefore, the concentration of $Mg^{2+}$ was studied in this example.

T7 RNA polymerase mix from NEB and Yeason were used for testing with concentrations of $Mg^{2+}$ at 4, 10, 16, 32, 35, 38, 41, and 44 mM, respectively. The reaction conditions and system can refer to the section of the in vitro transcription system in this example.

Figure 27:
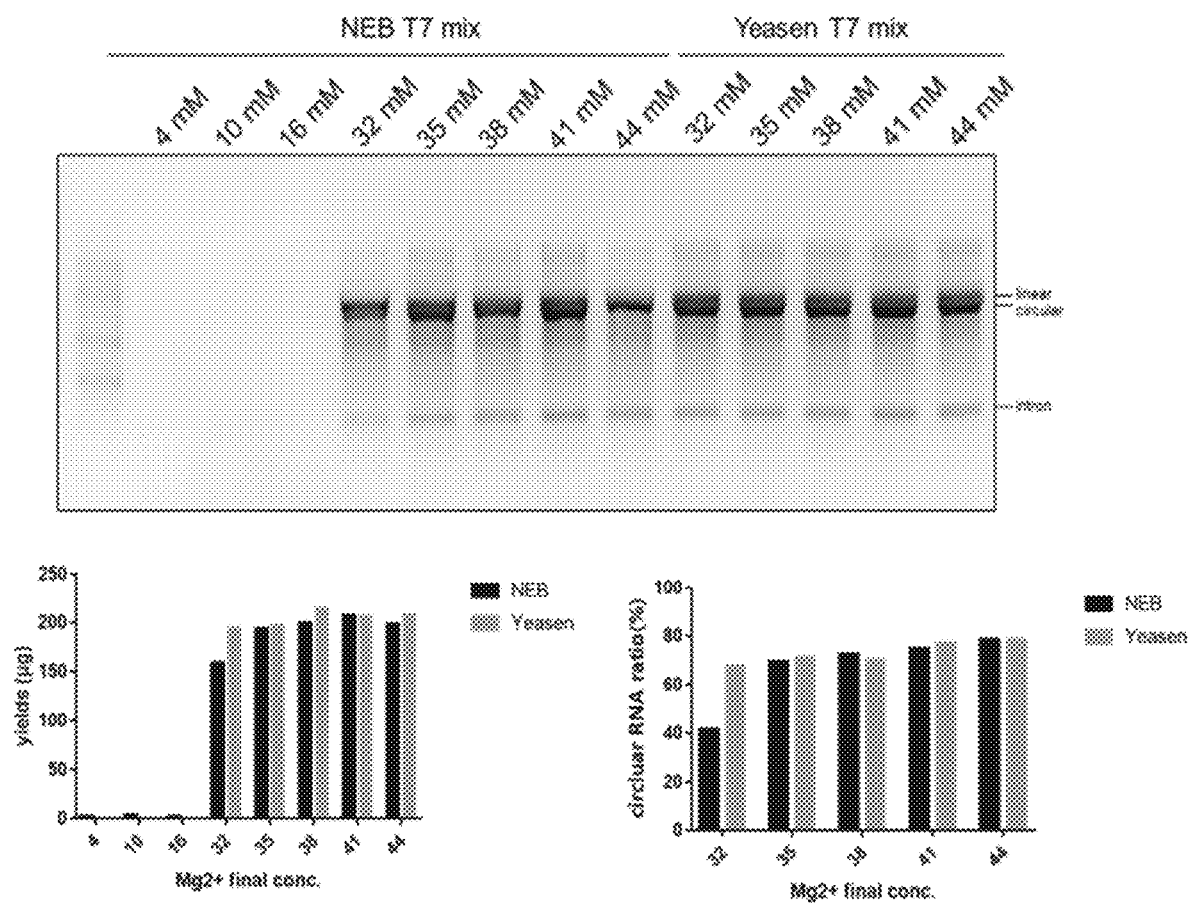
FIG. 27 shows an exemplary optimization result of a concentration of Mg$^{2+}$ in reaction products generated in an in vitro transcription reaction according to some embodiments of the present disclosure.
Figure 28:
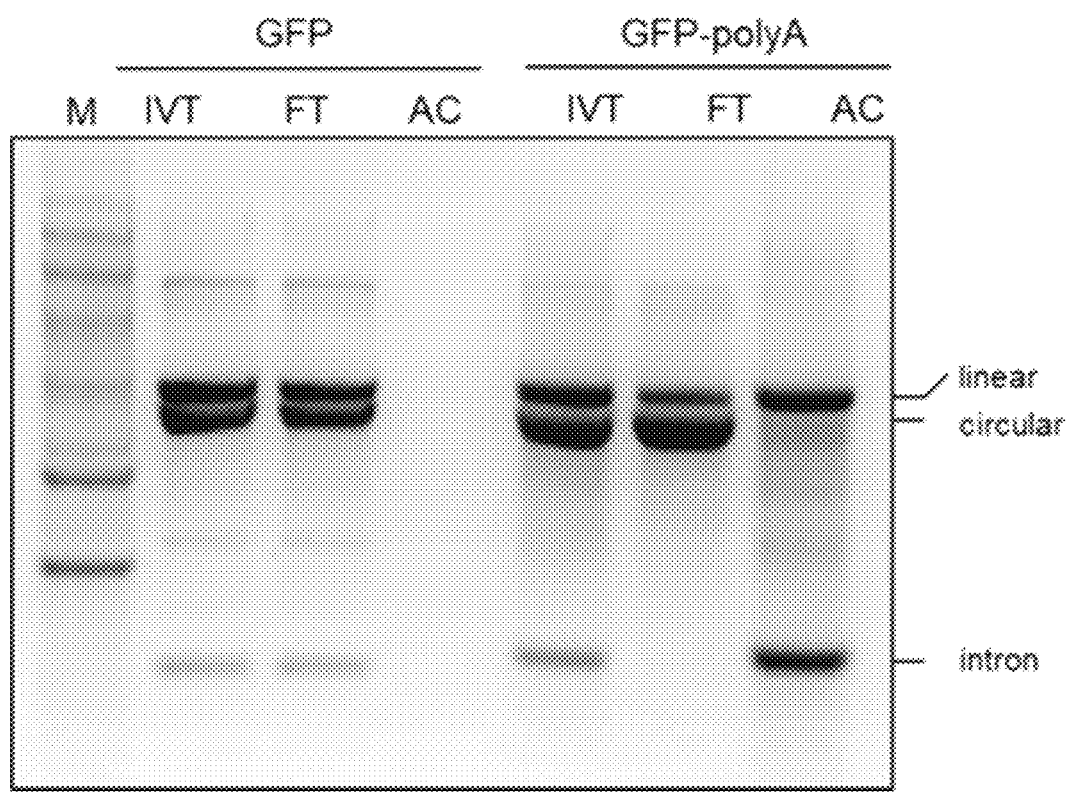
FIG. 28 shows a purification result of a circular RNA according to some embodiments of the present disclosure.

The result indicated that when the concentration of $Mg^{2+}$ is below 32 mM, almost no RNA was produced in the IVT reaction (as shown in FIG. 27). When the concentration of $Mg^{2+}$ is between 32-44 mM, RNA was produced in the IVT reaction, and in a 20 μl IVT reaction, the proportion of the circular RNA was 160-200 μg, and a proportion of the circular RNA ranged from 65% to 80%. As the increase of the concentration of $Mg^{2+}$, the proportion of the circular RNA was gradually increased (as shown in FIG. 28).

Example 6 the Affinity Purification of the Circular RNA

In this example, oligo dT affinity beads were used to purify the circular RNA. The purification of circular RNA is mainly carried out using SEC or other methods based on different molecular weights. However, due to the small difference in molecular weight between a circular RNA and a precursor linear RNA, the circular RNA and the precursor linear RNA cannot be separated well, resulting in poor purification efficiency of the circular RNA. In the present disclosure, a polyA sequence with a length of 29 nt was added to a front fragment of an intron fragment. After the in vitro transcription and the circularization reaction were finished, intron fragments of the byproduct during linearization and circularization of the precursor linear RNA were both including the polyA sequence with a length of 29 nt, which can be combined to affinity beads or fillers including oligo dT, while the circular RNA molecules without oligo dT cannot combine with affinity beads or fillers. Through the interaction between oligo dT and polyA, the affinity purification was carried out to obtain highly purified circular RNA in the flow cytometry. The specific steps are shown as follows:

(1) 50 μg IVT products was completed to 100 μl, and the 100 μl IVT products was performed a denaturation at 70° C. for 5 min, and was immediately cooled on ice;
(2) The oligo dT affinity beads were gently mixed, and 100 μl oligo dT affinity beads were added into a 1.5 ml EP tube to remove the liquid by using a magnetic holder;
(3) 200 μl combination liquid was added into the affinity beads, and were gently mixed well, and a magnetic holder was used to absorb excess liquid;
(4) Step (3) was repeated once;
(5) 100 μl combination liquid was added into the affinity beads, and the denatured RNA obtained from step (1) was added to the affinity bead suspension, and was slowly incubated at room temperature in a vertical mixer for 30 min;
(6) The EP tube was placed on the magnetic holder, the mixed liquid (flow through liquid) was drawn to a new EP tube. The liquid in the new EP tube included circular RNA components, 100 μl 7.5M LiCl was added and mixed well, and then was precipitated at (−20° C.) for 30 min;
(7) 200 μl cleaning solution was used to clean the affinity beads twice;
(8) The residual liquid was removed from the EP tube by suction;
(9) 15 μl RNase-free water was added to the affinity beads to elute the RNA bound to affinity beads at 70° C., and the RNA in this tube mainly consisted of prerequisite linear RNA and intron fragments of circularization byproduct;
(10) The liquid obtained in step (6) was centrifuged at 12000 rpm and 4° C. for 10 minutes, and the supernatant was discarded;
(11) 75% ethanol was used to wash the product obtained in step (10), the waste liquid was discarded, and the precipitate was dried at room temperature;
(12) 30 μl RNase-free water was added into the precipitate to dissolve the RNA.

Following the above steps, in this example, affinity beads with oligo dT were used for testing. The test result was shown in FIG. 28. When the DNA molecule included a product of 29 nt poly A (GFP-polyA) before the intron fragment, linear RNA and intron fragment in the reaction products of the in vitro transcription reaction were enriched due to the oligo dT affinity beads, while circRNA molecules were not adsorbed by the oligo dT affinity beads due to affinity, and there were no circRNA molecules present in an affinity column. The content of linear RNA and intron fragment in the flow-through (FT) (liquid) from the affinity column was greatly reduced, thus the circRNA was enriched in the FT. When the DNA molecule did not include 29 nt poly A before the intron fragment, the linear RNA and the intron fragment RNA in the reaction products from the in vitro transcription reaction were not adsorbed by the oligo dT affinity beads due to affinity, causing the circRNA not to be enriched in the FT. The above result indicated that the circular RNA can be purified by inserting poly A fragment into the DNA molecule and using affinity chromatography (AC, also referred to as affinity adsorption) to obtain highly purified circular RNAs.

Example 7 Enriching the Circular RNA Using the RNase R Enzyme

1. Enriching the Circular RNA Using the RNase R Enzyme

RNase R enzyme is a 3'-5' ribonucleic acid exonuclease that can digest almost all linear RNAs. In the system of circular RNA generation mediated by one-step transesterification reaction, precursor linear RNAs, circular RNA, and intron fragments of reaction byproduct were included. Both the precursor linear RNA and the intron fragments of reaction byproduct were linear RNAs, so the RNase R enzyme may be used to degrade these two linear RNA components, thereby enriching the circular RNA.

In this example, steps of enriching the circular RNA components using the RNase R enzyme are described based on the 30 μg IVT products. The reaction system is shown as follows:

| | |
|---|---|
| IVT products | 30 μg |
| 10× reaction buffer | 10 μl |
| RNase R enzyme (20 U/μl) | 1 μl |
| H₂O | up to 100 μl |

A pipette was used to mix the above substances well, the mixture was digested at 42° C. for 30 min.

Recovery of the Circular RNA

An RNA recovery kit was used to recover the enriched RNA, RNase-free water was added to elute, and a concentration of the RNA was measured.

1. Performing a Design of Experiment (DoE) on the RNase R Reaction System

The factors that affect RNase R digestion mainly include: the amount of input RNA, the amount of used RNase R enzyme, the reaction time, and the reaction temperature. Therefore, a DoE was performed by using these four factors, and a half fraction of DoE was chosen.

Based on experience, the amount of RNA used in this example was 30 μg and 100 μg. The reaction time was determined as 30 min and 60 min, the reaction temperatures were selected as 37° C. and 42° C., and the usage of RNase R were selected as 10 U and 30 U for testing.

Factor design was conducted using a minitab19 software, and half fraction of DoE was performed. A total of 8 sets of tests were conducted, as shown in Table 2

TABLE 2

A table of DoE

| Std Order | Run Order | Center point | Block | RNA | RNase R | Time | Temperature |
|---|---|---|---|---|---|---|---|
| 6 | 1 | 1 | 1 | 100 | 10 U | 60 | 37 |
| 3 | 2 | 1 | 1 | 30 | 30 U | 30 | 42 |
| 1 | 3 | 1 | 1 | 30 | 10 U | 30 | 37 |
| 4 | 4 | 1 | 1 | 100 | 30 U | 30 | 37 |
| 8 | 5 | 1 | 1 | 100 | 30 U | 60 | 42 |
| 7 | 6 | 1 | 1 | 30 | 30 U | 60 | 37 |
| 5 | 7 | 1 | 1 | 30 | 10 U | 60 | 42 |
| 2 | 8 | 1 | 1 | 100 | 10 U | 30 | 42 |

Figure 29:
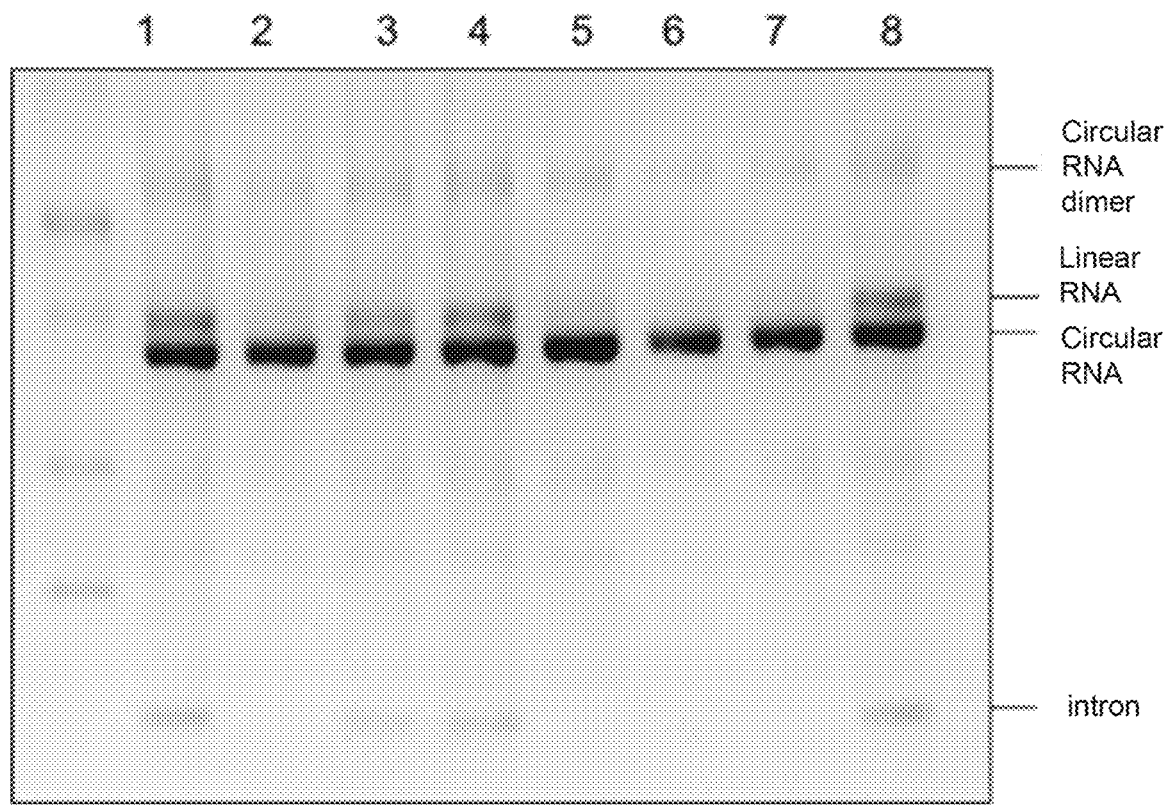
FIG. 29 shows an exemplary result of a gel electrophoresis with digestion products of RNase R according to some embodiments of the present disclosure.
Figure 30:
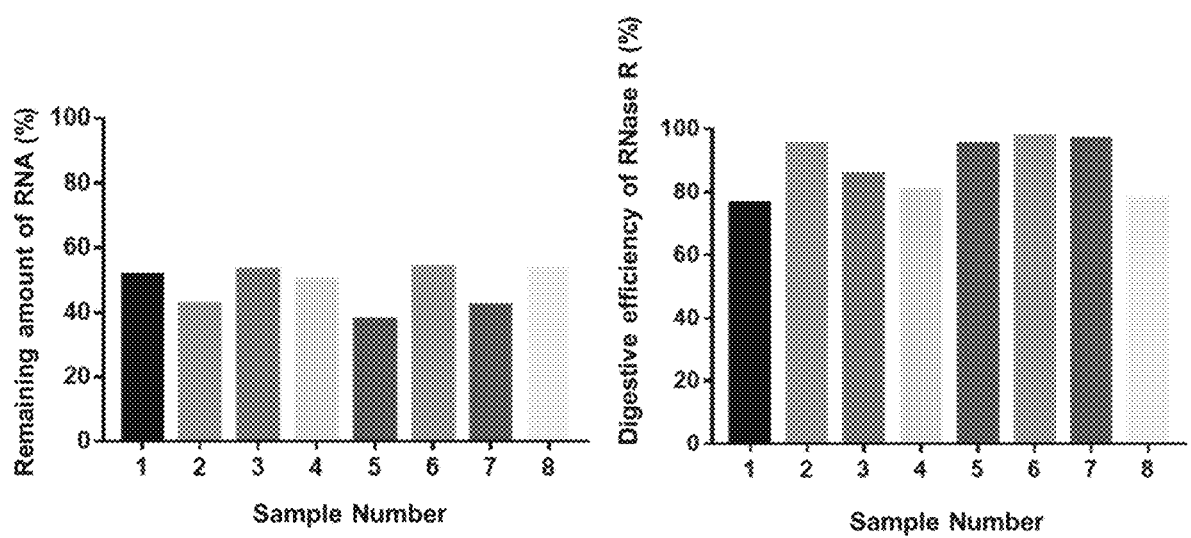
FIG. 30 shows an exemplary quantitative result of digestion products of RNase R according to some embodiments of the present disclosure.

The gel electrophoresis was used to detect the quality of generated RNA (as shown in FIG. 29), and image J was used to identify the proportion of the circular RNA (as shown in FIGS. 29 and 30). In this example, two methods were used to quantify the effect of RNase R enzyme, namely a remaining amount of RNA and a digestion efficiency of RNase R. The remaining amount of RNA reflects a relative residual RNA amount after the digestion with the RNase R enzyme, and the calculation formula is: RNA recovery after digestion/total digested RNA amount*100%; The digestion efficiency of the RNase R reflects the proportion of circular RNA after the digestion with the RNase R enzyme, and the calculation formula (grayscale quantification) is: circular RNA/(linear RNA+circular RNA)*100%.

The results showed that for sample numbers 1, 3, 6, and 8, there was more RNA remaining, indicating that RNase R degraded less RNA and retained more RNA in the system. The digestion efficiencies of the RNase R were higher after reaction of sample numbers 5, 6, and 7 (as shown in FIGS. 29 and 30).

Figure 31:
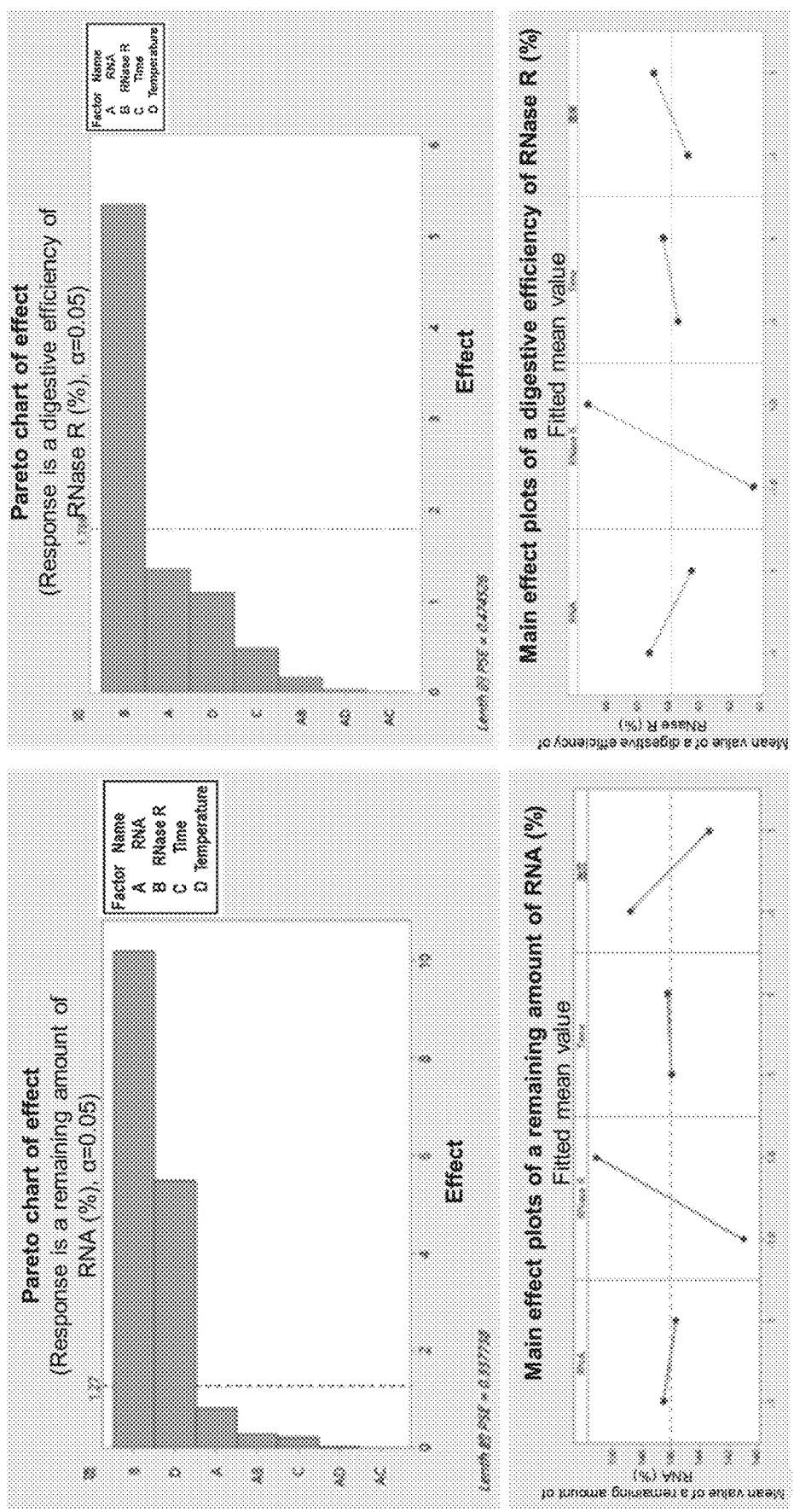
FIG. 31 shows an exemplary Pareto effect according to some embodiments of the present disclosure.

Through factor analysis of the two results, it can be found from the Pareto chart of effect that the amount of RNase R input and reaction temperature mainly affect the remaining amount of RNA after the digestion with the RNase R enzyme. The amount of RNase R input mainly affects the digestion efficiency of RNase R. There was a significant positive correlation between the input of RNase R and the result among these four factors (As shown in FIG. 31).

Example 8 Optimization of a Purification Process

In the process discussed above, the IVT products needs to be purified or liquid-replaced before performing a digestion with the RNase R, which leads to redundancy in the process and affects the yield of the circular RNA (adding one step of the route may result in RNA loss). When using RNase R to directly digest the linear RNA in IVT products, it is necessary to consider the effect of factors such as $Mg^{2+}$ in the reaction system on RNase R. The optimal concentration of $Mg^{2+}$ for RNase R may be 0.1-1 mM, while the final concentration of $Mg^{2+}$ in the IVT system was 46 mM. Therefore, chelation of excessive $Mg^{2+}$ is necessary to facilitate the digestion with the RNase R (as shown in FIG. 32).

In this example, EDTA was directly added to the IVT products for chelating $Mg^{2+}$, with concentrations of EDTA of 44, 30, 20, 10, and 0 mM, respectively. Then, the RNase R was added to the system for digestion, and the digestion products were analyzed after recovery.

Figure 33:
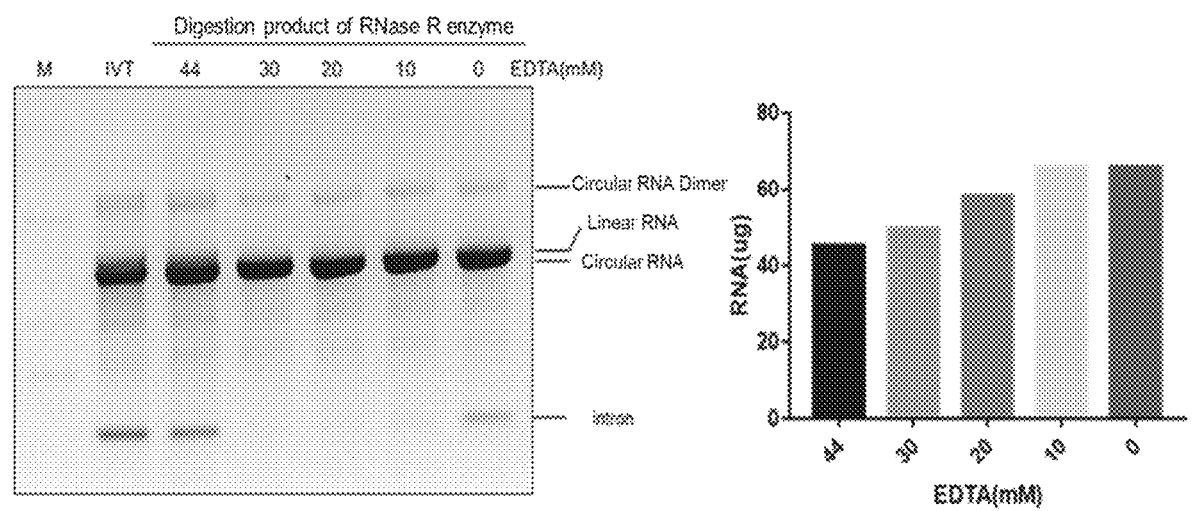
FIG. 33 shows an exemplary effect on a digestion efficiency of RNase R by adding different amount of EDTA into reaction products generated in an in vitro transcription reaction according to some embodiments of the present disclosure.

From the gel plot (As shown in FIG. 33), it can be seen that when 30-10 mM of EDTA is added to the IVT system, the activity of RNase R is not affected, while when the concentration of EDTA is 44 mM or without EDTA, RNase R cannot degrade the linear RNA well (as shown in FIG. 33).

Figure 34:
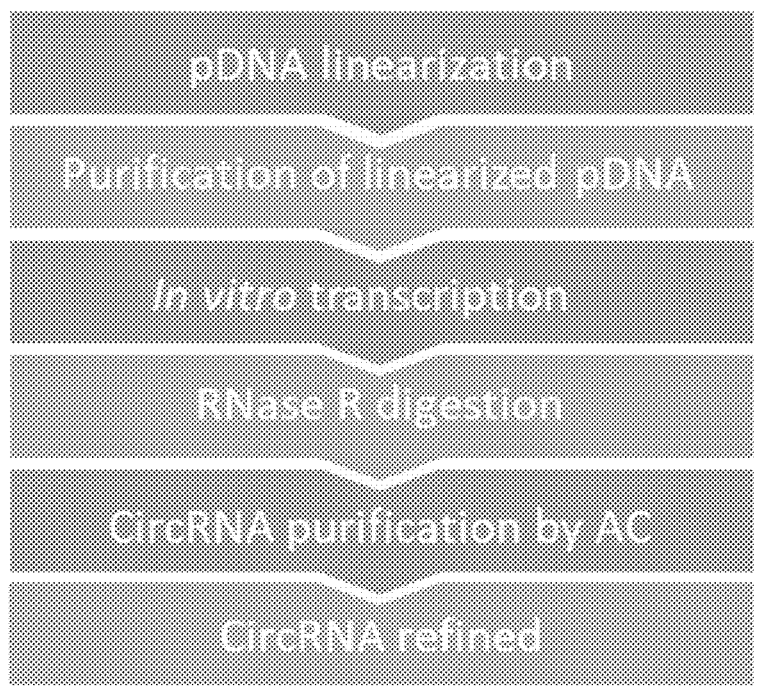
FIG. 34 shows an exemplary process of preparing a circular RNA according to some embodiments of the present disclosure.

Finally, based on the above optimization of the operations in each process (as shown in FIG. 34), the following steps to obtain high-purity circular RNA were summarized: plasmid linearization, purification of linearized plasmid, the in vitro transcription, digestion with RNase R, circular RNA purification by affinity chromatography, refining, etc.

The potential beneficial effects of embodiments of the present disclosure may include, but may not be limited to: (1) by providing a DNA molecule (e.g. a vector) for the in vitro transcription to make a circular RNA, and a method for preparing the circular RNA by the in vitro transcription reaction through a one-step esterification reaction of the DNA molecule or the vector. Moreover, without homology arm sequences, direct circularization can be achieved, thereby reducing the raw materials required for an in vitro circularization, reducing costs, and improving the circularization efficiency. The main component produced by the in vitro transcription reaction may be circular RNA, which may not cause changes in the structural conformation of the RNA after circularization. (2) By providing a DNA molecule (e.g. a vector) for making a circular RNA, the circular RNA can be purified by affinity purification using oligo dT affinity beads, and the purification efficiency in such way is high.

It should be noted that different embodiments may produce different beneficial effects. In different embodiments, the possible beneficial effects may be any one or a combination of the above, or any other possible beneficial effects may be obtained.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of the present disclosure are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A DNA molecule for making a circular RNA, comprising elements operably connected and arranged, from a 5' to 3' direction, in the following order:

(a) a full-length intron having the nucleotide sequence of SEQ ID NO: 1;

(b) an E2 fragment which includes a downstream exon of the full-length intron, the E2 fragment having the nucleotide sequence of SEQ ID NO: 2;

(c) an internal ribosome entry site (IRES) fragment that is from Coxsackie virus B3 (CVB3);

(d) a target DNA sequence that encodes a target peptide; and (e) an E1 fragment which includes an upstream exon of the full-length intron, the E1 fragment having the nucleotide sequence of SEQ ID NO: 8; wherein:

the full-length intron, the downstream exon, and the upstream exon are from a pre-tRNA$_{Leu}$ gene of genus *Anabaena;*

3' end of the E1 fragment is configured to produce a hydroxyl group in an in vitro transcription reaction, wherein the hydroxyl group is formed by using a restriction endonuclease cleavage when preparing an in vitro transcription template with the DNA molecule, followed by the in vitro transcription reaction, and the in vitro transcription template includes the full-length intron, the E2 fragment, the target DNA sequence, and the E1 fragment;

the hydroxyl group is capable of initiating splicing in a one-step transesterification reaction at a splice site between RNA fragments transcribed from the full-length intron and the E2 fragment in a linear RNA that is produced from the DNA molecule in the in vitro transcription reaction, such that the linear RNA is configured to self-circularize to produce the circular RNA; and the DNA molecule does not include any intron sequence at the 3' end of the E1 fragment.

2. The DNA molecule of claim 1, wherein the IRES fragment is transcribed to an RNA molecule that is capable of recruiting ribosomes for a translation reaction to obtain the target peptide.

3. The DNA molecule of claim 1, wherein the DNA molecule does not include a 5' homology arm sequence or a 3' homology arm sequence positioned between the E2 fragment and the E1 fragment when the length of the target DNA sequence that encodes the target peptide is less than 2000 nt.

4. The DNA molecule of claim 1, wherein the pre-tRNA$_{Leu}$ gene has the nucleotide sequence shown in SEQ ID NO. 19.

5. The DNA molecule of claim 1, further comprising a poly A sequence of at least 29 consecutive A bases before the full-length intron.

6. The DNA molecule of claim 1, wherein the DNA molecule is a vector.

* * * * *

```
                            SEQUENCE LISTING

Sequence total quantity: 20
SEQ ID NO: 1            moltype = DNA  length = 249
FEATURE                 Location/Qualifiers
source                  1..249
                        mol_type = genomic DNA
                        organism = Anabaena sp.
SEQUENCE: 1
aaataattga gccttaaaga agaaattctt taagtggatg ctctcaaact cagggaaacc    60
taaatctagt tatagacaag gcaatcctga gccaagccga agtagtaatt agtaagttaa   120
caatagatga cttacaacta atcggaaggt gcagagactc gacgggagct accctaacgt   180
caagacgagg gtaaagagag agtccaattc tcaaagccaa taggcagtag cgaaagctgc   240
aagagaatg                                                           249

SEQ ID NO: 2            moltype = DNA  length = 51
FEATURE                 Location/Qualifiers
source                  1..51
                        mol_type = genomic DNA
                        organism = Anabaena sp.
SEQUENCE: 2
aaaatccgtt gaccttaaac ggtcgtgtgg gttcaagtcc ctccaccccc a              51

SEQ ID NO: 3            moltype = DNA  length = 40
FEATURE                 Location/Qualifiers
source                  1..40
                        mol_type = genomic DNA
                        organism = Anabaena sp.
SEQUENCE: 3
aaaatccgtt gaccttaaac ggtcgtgtgg gttcaagtcc                           40

SEQ ID NO: 4            moltype = DNA  length = 30
FEATURE                 Location/Qualifiers
source                  1..30
                        mol_type = genomic DNA
                        organism = Anabaena sp.
SEQUENCE: 4
aaaatccgtt gaccttaaac ggtcgtgtgg                                      30

SEQ ID NO: 5            moltype = DNA  length = 20
FEATURE                 Location/Qualifiers
source                  1..20
                        mol_type = genomic DNA
                        organism = Anabaena sp.
SEQUENCE: 5
aaaatccgtt gaccttaaac                                                 20

SEQ ID NO: 6            moltype = DNA  length = 221
FEATURE                 Location/Qualifiers
source                  1..221
                        mol_type = other DNA
                        organism = synthetic construct
SEQUENCE: 6
tcaagatccg ccaacacatc gaggacggca gcgtgcagct cgccgaccac taccagcaga    60
acacccccat cggcgacggc cccgtgctgc tgcccgacaa ccactacctg agcacccagt   120
ccgccctgag caaagacccc aacgagaagc gcgatcacat ggtcctgctg gagttcgtga   180
ccgccgccgg gatcactctc ggcatggacg agctgtacaa g                       221

SEQ ID NO: 7            moltype = DNA  length = 1118
FEATURE                 Location/Qualifiers
source                  1..1118
                        mol_type = other DNA
                        organism = synthetic construct
SEQUENCE: 7
actggagttc tgtgacagga gccaccatga aagtattaag aggacaaatc gtgcaaggtg    60
tggtatggct gctactagta actggggcac aaggccggct agcctgcaaa gaagactaca   120
ggtacgcaat atcatcgacc gacgaaatag ggctactcgg ggccggaggt ctcaccacca   180
cctggaaaga atacaaccac gacttgcaac tgaacgacgg gaccgtcaaa gccagttgcg   240
tggcaggttc cttcaaagtc acagcactca acgtggtcag taggaggtac ttggcatcat   300
tgcacaaaaa agctctaccc acttccgtga cattcgaact cctgttcgac gggaccaacc   360
```

```
catcaactga agaaatggga gacgacttcc ggtccgggct gtgccgttc  gacacgagtc    420
ctgtcgtcaa aggaaaatac aacacaacct tgttgaacgg tagtgctttc tacctcgtct    480
gcccaatagg gtggacgggt gtcatagaat gcacagcagt gagcccaaca actctgagaa    540
cagaagtggt aaaaaccttc aggagagaca aaccctttccc gcacagaatg gactgtgtga   600
ccaccacagt ggaaaacgaa gacttattct actgtaaatt gggggggcaac tggacatgtg   660
tgaaaggtga accagtggtc tacacgggg  gggtagtaaa acaatgcaga tggtgtggct    720
tcgacttcga cgggcccgac ggactcccgc actacccccat aggtaaatgc atcttggcaa   780
acgaaacagg ttacagaata gtagactcaa cggactgtaa cagagacggc gtcgtaatca    840
gcacagaagg gagtcacgaa tgcttgatcg gtaacacaac tgtcaaagtg cacgcatcag    900
acgaaagact gggccctatg ccatgcagac ccaaagaaat cgtctctagt gcaggacctg    960
taatgaaaac ttcctgtaca ttcaactaca caaaaacttt gaaaaacagg tactacgaac   1020
ccagggacag ctacttccaa caatacatgc tcaaaggcga ataccaatac tggttcgacc   1080
tggacgcgcg ctgaccgcca ctcagactact tcgcatga                          1118

SEQ ID NO: 8         moltype = DNA    length = 15
FEATURE              Location/Qualifiers
source               1..15
                     mol_type = genomic DNA
                     organism = Anabaena sp.
SEQUENCE: 8
agacgctacg gactt                                                       15

SEQ ID NO: 9         moltype = DNA    length = 10
FEATURE              Location/Qualifiers
source               1..10
                     mol_type = genomic DNA
                     organism = Anabaena sp.
SEQUENCE: 9
ctacggactt                                                             10

SEQ ID NO: 10        moltype = DNA    length = 15
FEATURE              Location/Qualifiers
source               1..15
                     mol_type = other DNA
                     organism = synthetic construct
SEQUENCE: 10
agacgctacg gagtt                                                       15

SEQ ID NO: 11        moltype = DNA    length = 15
FEATURE              Location/Qualifiers
source               1..15
                     mol_type = other DNA
                     organism = synthetic construct
SEQUENCE: 11
agacgctacg gattt                                                       15

SEQ ID NO: 12        moltype = DNA    length = 20
FEATURE              Location/Qualifiers
source               1..20
                     mol_type = other DNA
                     organism = synthetic construct
SEQUENCE: 12
cgccggaaac gcaatagccg                                                  20

SEQ ID NO: 13        moltype = DNA    length = 22
FEATURE              Location/Qualifiers
source               1..22
                     mol_type = other DNA
                     organism = synthetic construct
SEQUENCE: 13
cggctattat gcgttaccgg cg                                               22

SEQ ID NO: 14        moltype = DNA    length = 741
FEATURE              Location/Qualifiers
source               1..741
                     mol_type = genomic DNA
                     organism = Coxsackie virus B3
SEQUENCE: 14
ttaaaacagc ctgtgggttg atcccaccca caggcccatt gggcgctagc actctggtat     60
cacggtacct ttgtgcgcct gttttatacc ccctcccca  actgtaactt agaagtaaca    120
cacaccgatc aacagtcagc gtggcacacc agccacgttt tgatcaagca cttctgttac    180
cccggactga gtatcaatag actgctcacg cggttgaagg agaaagcgtt cgttatccgg    240
ccaactactt cgaaaaacct agtaacaccg tggaagttgc agagtgtttc gctcagcact    300
accccagtgt agatcaggtc gatgagtcac cgcattccac acgggcgacc gtgcggtgg    360
ctgcgttggc ggcctgccca tgggaaaacc catgggacgc tctaatacag acatggtgcg    420
aagagtctat tgagctagtt ggtagtcctc cggcccctga atgcggctaa tcctaactgc    480
ggagcacaca ccctcaagcc agagggcagt gtgtcgtaac gggcaactct gcagcggaac    540
cgactacttt gggtgtccgt gtttcatttt attcctatac tggctgctta tggtgacaat    600
tgagagatct ttaccatata gctattggat tggccatccg gtgactaata gagctattat    660
```

```
atatccctt  gttgggttta  taccacttag  cttgaaagag  gttaaaacat  tacaattcat   720
tgttaagttg  aatacagcaa  a                                              741
```

SEQ ID NO: 15            moltype = DNA   length = 720
FEATURE                  Location/Qualifiers
source                   1..720
                         mol_type = other DNA
                         organism = synthetic construct
SEQUENCE: 15
```
atggtgagca  agggcgagga  gctgttcacc  ggggtggtgc  ccatcctggt  cgagctggac   60
ggcgacgtaa  acggccacaa  gttcagcgtg  tccggcgagg  gcgagggcga  tgccacctac  120
ggcaagctga  ccctgaagtt  catctgcacc  accggcaagc  tgcccgtgcc  ctggcccacc  180
ctcgtgacca  cccctgaccta cggcgtgcag  tgcttcagcc  gctaccccga  ccacatgaag  240
cagcacgact  tcttcaagtc  cgccatgccc  gaaggctacg  tccaggagcg  caccatcttc  300
ttcaaggacg  acggcaacta  caagacccgc  gccgaggtga  agttcgaggg  cgacaccctc  360
gtgaaccgca  tcgagctgaa  gggcatcgac  ttcaaggagg  acggcaacat  cctggggcac  420
aagctggagt  acaactacaa  cagccacaac  gtctatatca  tggccgacaa  gcagaagaac  480
ggcatcaagg  tgaacttcaa  gatccgccac  aacatcgaag  acggcagcgt  gcagctgccc  540
gaccactacc  agcagaacac  ccccatcggc  gacggccccg  tgctgctgcc  cgacaaccac  600
tacctgagca  cccagtccgc  cctgagcaaa  gaccccaacg  agaagcgcga  tcacatggtc  660
ctgctggagt  tcgtgaccgc  cgccgggatc  actctcggca  tggacgagct  gtacaagtga  720
```

SEQ ID NO: 16            moltype = DNA   length = 20
FEATURE                  Location/Qualifiers
source                   1..20
                         mol_type = other DNA
                         organism = synthetic construct
SEQUENCE: 16
```
ggccagtgaa  ttgtaatacg                                                   20
```

SEQ ID NO: 17            moltype = DNA   length = 20
FEATURE                  Location/Qualifiers
source                   1..20
                         mol_type = other DNA
                         organism = synthetic construct
SEQUENCE: 17
```
aactccgtag  cgtctcgccg                                                   20
```

SEQ ID NO: 18            moltype = DNA   length = 1877
FEATURE                  Location/Qualifiers
source                   1..1877
                         mol_type = genomic DNA
                         organism = T4 phage
SEQUENCE: 18
```
atgaaacaat  accaagattt  aattaaagac  atttttgaaa  atggttatga  aaccgatgat   60
cgtacaggca  caggaacaat  tgctctgttc  ggtactaaat  tacgctggga  tttaactaaa  120
ggttttcctg  cggtaacaac  taagaagctc  gcctggaaca  cttgcattgc  tgagctaata  180
tggttttttat caggaagcac  aaatgtcaat  gatttacgat  taattcaaca  cgattcgtta  240
atccaaggca  aaacagtctg  ggatgaaaat  tacgaaaatc  aagcaaaaga  tttaggatac  300
catagcggta  aacttggtcc  aatttatgga  aaacagtggc  gtgattttgg  tggtgtagac  360
caaattatag  aagttattga  tcgtattaaa  aaactgccaa  atgataggcg  tcaaattgtt  420
tctgcatgga  atccagctga  acttaaatat  atggcattac  cgccttgtca  tatgttctat  480
cagtttaatg  tgcgtaatgg  ctattttggat  ttgcagtggt  atcaacgctc  agtagatgtt  540
ttcttgggtt  aattgaggcc  tgagtataag  gtgacttata  cttgtaatct  atctaaacgg  600
ggaacctctc  tagtagacaa  tcccgtgcta  aattgtagaa  ctgcccttta  ataaatactt  660
ctatatttaa  agaggtattt  atgaaaagcg  gaatttatca  gattaaaaat  acttaaaaca  720
ataaagtata  tgtaggaagt  gctaaagatt  ttgaaaagag  atggaagagg  catttttaag  780
atttagaaaa  aggatgccat  tcttctataa  aacttcagag  gtcttttaac  aaacatggta  840
atgtgtttga  atgttctatt  ttggaagaaa  ttccatatga  gaaagatttg  attattgaac  900
gagaaaattt  ttggattaaa  gagcttaatt  ctaaaattaa  tggatacaat  attgctgatg  960
caacgtttgg  tgatacatgt  tctacgcatc  cattaaaaga  agaaattatt  aagaaacgtt 1020
ctgaaactgt  taaagctaag  atgcttaaac  ttggacctga  tggtcggaaa  gctctttaca 1080
gtaaacccgg  aagtaaaaac  gggcgttgga  atccagaaac  cctaagtttt  tgtaagtgcg 1140
gtgttcgcat  acaaaattct  gcttatactt  gtagtaaatg  cagaaatgct  tcaggtgaaa 1200
ataattcatt  ctttaatcat  aagcattcag  acataactaa  atctaaaata  tcagaaaaga 1260
tgaaaggtaa  aaagcctagt  aatattaaaa  agatttcatg  tgatggggtt  attttttgatt 1320
gtgcagcaga  tgcagctaga  catttaaaaa  tttcgtctgg  attagttact  tatcgtgtaa 1380
aatctgataa  atggaattgg  ttctacataa  atgcctaacg  actatccctt  tggggagtag 1440
ggtcaagtga  ctcgaaacga  tagacaactt  gctttaacaa  gttggagata  tagtctgctc 1500
tgcatggtga  catgcagctg  gatataattc  cggggtaaga  ttaacgacct  tatctgaaca 1560
taatgctacc  gttaatattt  gcgtcatatg  ctacgttagt  tcatattgta  gctaagatgt 1620
gtaatcttat  tccaggggat  ttgatatttt  ctggtggtaa  tactcatatc  tatatgaatc 1680
acgtagaaca  atgtaaagaa  attttgaggc  gtgaacctaa  agagctttgt  gagctggtaa 1740
taagtggtct  accttataaa  ttccgatatc  tttactaaa  agaacaatta  aaatatgttc 1800
ttaaacttag  gcctaaagat  ttcgttctta  acaactatgt  atcacaccct  cctattaaag 1860
gaaagatggc  ggtgtaa                                                   1877
```

SEQ ID NO: 19            moltype = DNA   length = 334
FEATURE                  Location/Qualifiers -continued

```
source                  1..334
                        mol_type = genomic DNA
                        organism = Anabaena sp.
SEQUENCE: 19
tgggggtgga gggacttgaa cccacacgac cgtttaaggt caacggattt tcattctccc  60
gcagctttcg ctactgccta ttggctttga gaattggact ctctctttac cctcgtcttg  120
acgttagggt agctcccgtc gagtctctgc accttccgat tagctgtaag ttatctgttg  180
ttaacttact aattactact tcggcttggc tcaggattgc cttgtctata gctagattta  240
ggtttccctg agtttgagag catccactta aagaatttct tctctaaggc tcaattattt  300
aagtccgtag cgtctaccat tccgccacac cccc                              334

SEQ ID NO: 20           moltype = DNA  length = 82
FEATURE                 Location/Qualifiers
source                  1..82
                        mol_type = genomic DNA
                        organism = Anabaena sp.
SEQUENCE: 20
cgcatgacgg ctattatgcg ttaccggcga gacgctacgg acttaaaatc cgttgacctt  60
aaacgcgccg gaaacgcaat ag                                           82
```